US006210667B1

(12) United States Patent
Reed

(10) Patent No.: US 6,210,667 B1
(45) Date of Patent: Apr. 3, 2001

(54) BACTERIAL FIBRIN-DEPENDENT PLASMINOGEN ACTIVATOR

(75) Inventor: Guy L. Reed, Winchester, MA (US)

(73) Assignee: The President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 09/211,542

(22) Filed: Dec. 15, 1998

Related U.S. Application Data

(60) Provisional application No. 60/069,497, filed on Dec. 15, 1997.

(51) Int. Cl.[7] .............................. A61K 38/48; C12N 9/70

(52) U.S. Cl. ...................... 424/94.64; 435/216; 435/325; 530/350; 530/381

(58) Field of Search ...................... 424/94.64; 435/216, 435/325; 530/350, 381

(56) References Cited

U.S. PATENT DOCUMENTS

| | | | |
|---|---|---|---|
| 4,745,056 | 5/1988 | Guterman et al. | 435/68 |
| 4,820,639 | 4/1989 | Gehrke | 435/68 |
| 5,011,686 | 4/1991 | Pang | 424/94.1 |
| 5,187,098 | 2/1993 | Malke et al. | 435/320.1 |
| 5,240,845 | 8/1993 | Fujii et al. | 435/216 |
| 5,854,049 | * 12/1998 | Reed | 435/216 |

FOREIGN PATENT DOCUMENTS

| | | | |
|---|---|---|---|
| 0146050A2 | 6/1985 | (EP) | C12N/11/02 |
| 0397366A1 | 11/1990 | (EP) | C12N/15/58 |
| 0407942A2 | 1/1991 | (EP) | C12N/15/57 |
| WO94/07992 | 10/1993 | (WO) | C12N/1/00 |
| WO96/41883 | 6/1996 | (WO) | C12N/15/31 |

OTHER PUBLICATIONS

Fletcher, A., "The Clearance of Heterologous Protein From the Circulation of Normal and Immunized Man[1,2]", *J Clin Invest* 37:1306–1315 (1959).
Kline, D. et al., "Proactivator Function of Human Plasmin as Shown by Lysine Esterase Assay", *J. Biol. Chem.* 236:2807–2812 (1961).
Wulf et al., "Studies on plasminogen. VIII. Species specificity of streptokinase", *Canadian Journal of Biochemistry*, vol. 47, 1969, pp. 927 931.
McClintock, D. et al., "The Mechanism of Activation of Human Plasminogen by Streptokinase", *Biochem. Biophys. Res.Commun.* 43:694–702 (1971).
Brockway, W. et al., "A Characterization of Native Streptokinase and Altered Streptokinase Isolated from a Juman Plasminogen Activator Complex", *Biochemistry*, vol. 13, No. 10, 1974, pp. 2063–2070.
Markus, G. et al., "Activator Activities of the Transient forms of the Human Plasminogen Streptokinase complex during its Proteolytic Conversion to the Stable Activator Complex", *J Biol Chem* 251:6495–6504 (1976).

Siefring, G. et al., "Interaction of Streptokinase with Plasminogen", *J Biol Chem.* 251:3913–20 (1976).
Wohl, R. et al., "Kinetics of Activation of Human Plasminogen by Different Activator Species at pH 7.4 and 37° C", *J. Biol. Chem.* 255:2005–2013 (1980).
Fears, R. et al., "Kinetic studies on the interaction of streptokinase and other plasminogen activators with plasminogen and fibrin", *Biochem. J.* 229:555–558 (1985).
Malke, H. et al., "Nucleotide sequence of the streptokinase gene from *Streptococcus equisimilis* H46A", Gene, 34 (1985). pp. 357–362.
Jackson et al., "Active Streptokinase from the Cloned Gene in *Streptococcus sanguis* Is without the Carboxyl–Terminal 32 Residues", *Biochemistry*, vol. 25, No. 1, 1986, pp. 108–114.
Reddy, K., "Streptokinase—biochemistry and Clinical Application", *Enzyme* 40:79–89 (1988).
Huang et al., "Heterogeneity of the Streptokinase Gene in Group A Streptococci", Infection and Immunity, Feb. 1989, pp. 502–506.
Huang, T. et al., "The streptokinase gene of group A streptococci: cloning, expression in *Escherichia coli*, and sequence analysis" *Mol. Microbio.* 3:197–205 (1989).
Lee et al., "Site–Specific Alteration of GLY–24 in Streptokinase: Its Effect on Plasminogen Activation", *Biochemical and Biophysical Research Communications*, vol. 165, No. 3, 1989, Dec. 29, 1989, pp. 1085–1090.
Reed et al., "Synergistic fibrinolysis: Combined effects of plasminogen activators and an antibody that inhibits $\alpha_2$–antiplasmin", *Proc. Natl. Acad. Sci. USA*, vol. 87, Feb. 1990, pp. 1114–1118.
Nakashima, A. et al., "Fibrin–dependent activation of plasminogen by a proteolytic digest of streptokinase", *Blood Coagulation and Fibrinolysis*, Aug. 1990, pp. 279–284.
Sherry, S., "Pharmacology of Anistreplase", *Clin Cardiol* 13:3–10 (1990).
Shi et al., "Activation of Human and Bovine Plasminogens by the Microplasmin and Streptokinase Complex", *Thrombosis Research*, vol. 58, No. 3, 1990, pp. 317–329.
McCoy, H. et al., "Streptokinases Produced by Pathogenic Group C Streptococci Demonstrate Species–Specific Plasminogen Activation", *The Journal of Infectious Diseases* 1991, pp. 515–521.

(List continued on next page.)

*Primary Examiner*—Rebecca E. Prouty
*Assistant Examiner*—Richard Hutson
(74) *Attorney, Agent, or Firm*—Bromberg & Sunstein LLP

(57) ABSTRACT

A pharmaceutical composition in a preferred embodiment comprises an isolated bacterial protein that induces fibrin-dependent plasminogen activation, and methods for dissolving blood clots in a subject use such a composition. Embodiments also include a nucleic acid encoding such a bacterial protein, a nucleic acid encoding such a bacterial protein as a fusion to another protein, an expression vector with the nucleic acid, and a host cell transformed with the expression vector.

11 Claims, 3 Drawing Sheets

OTHER PUBLICATIONS

Misselwitz, R. et al., "Limited proteolysis of streptokinase and properties of some fragments", *Int. J. Biol. Macromol.,* Apr. 1992, vol. 14.

Johnston, K. et al., "Analysis of the Variable Domain of the Streptokinase Gene from Streptococci Associated with Post–Streptococcal Glomerulonephritis", *New Perspectives on Streptococci and Streptococcal Infections,* Supplement 22, 1992, pp. 339–342.

Reed et al., "A Functional Analysis of the Antigenicity of Streptokinase Using Monoclonal Antibody Mapping and Recombinant Streptokinase Fragments", *The Journal of Immunology,* vol. 150, May 15, 1993, pp. 4407–4415.

Shi et al., "Interaction of Immobilized Human Plasminogen and Plasmin with Streptokinase", *Biochemical and Biophysical Research Communications,* vol. 195 No. 1, Aug. 31, 1993, pp. 192–200.

Ross et al., "The Effects of Tissue Plasminogen Activator, Streptokinase, or Both on Coronary–Artery Patency, Ventriculuar Function, and Survival After Acute Myocardial Infarction", *The New England Journal of Medicine,* Nov. 25, 1993, vol. 329, No. 22, pp. 1615–1622.

Malke, H. et al., "Polymorphism of the Streptokinase Gene: Implications for the Pathogenesis of Post–Streptococcal Glomerulonephritis", *Zbl. Bakt.* 278, pp. 246–257 (1993).

Shi, G. et al., "Function of streptokinase fragments in plasminogen activation", *Biochemical Journal,* Nov. 15, 1994, pp. 235–241.

Nowicki et al., "Characterization of a Novel Streptokinase Produced by *Streptococcus equisimilis* of Non–Human Origin", *Thrombosis and Hemostasis* 72(4), 1994, pp. 595–603.

Shishido, Y. et al., "Involvement of protease inhibitors in staphylokinase–induced fibrin–specific fibrinolysis", Biological and Pharmaceutical Bulletin, Dec. 1994.

Kapur, V. et al., "Molecular population genetic analysis of the streptokinase gene of *Streptococcus pyogenes;* mosaic alleles generated by recombination", *Molecular Microbiology,* 1995, pp. 509–519.

Parhami–Seren et al., "Mapping the Antigenic Regions of Streptokinase in Humans Before and After Streptokinase Therapy", *Molecular Immunology,* vol. 32, No. 10, 1995, pp. 717–724.

Reed et al., "Identification of a Plasminogen Binding Region in Streptokinase That Is Necessary for the Creation of a Functional Streptokinase—Plasminogen Activator Complex", *Biochemistry,* vol. 34, 1995, pp. 10266–10271.

Young et al., "Interaction of Streptokinase and Plasminogen", *The Journal of Biological Chemistry,* vol. 270 No. 49, Dec. 8, 1995, pp. 29601–29606.

Parrado et al., "The domain organization of streptokinase: Nuclear magnetic resonance, circular dichroism, and functional characterization of proteolytic fragments", *Protein Science* (1996), 5:693–704.

Parhami–Seren et al., "Structural Characterization of Immunodominant Regions of Streptokinase Recognized by Murine Monoclonal Antibodies", *Hybridoma* vol. 15, No. 3, 1996, pp. 169–176.

Lin et al., "Mutation of Lysines in a Plasminogen Binding Region of Streptokinase Identifies Residues Important for Generating a Functional Activator Complex", *Biochemistry* 1996, 35, pp. 16879–16885.

Parhami–Seren et al., "Sequences of Antigenic Epitopes of Streptokinase Identified via Random Peptide Libraries Displayed on Phage", *J. Mol. Biol.* (1997) 271, pp. 333–341.

International Search Report, Apr. 26, 1999.

* cited by examiner

SEQUENCE LISTING (1) GENERAL INFORMATION:

(iii) NUMBER OF SEQUENCES: 14

(2) INFORMATION FOR SEQ ID NO:1:

(i) SEQUENCE CHARACTERISTICS:
        (A) LENGTH: 2385 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..2385

(xi) SEQUENCE DESCRIPTION: SEQ ID NO:1:

```
ATG AAA ACT GAA GAA GGT AAA CTG GTA ATC TGG ATT AAC GGC GAT AAA        48
Met Lys Thr Glu Glu Gly Lys Leu Val Ile Trp Ile Asn Gly Asp Lys
 1               5                  10                  15

GGC TAT AAC GGT CTC GCT GAA GTC GGT AAG AAA TTC GAG AAA GAT ACC        96
Gly Tyr Asn Gly Leu Ala Glu Val Gly Lys Lys Phe Glu Lys Asp Thr
                20                  25                  30

GGA ATT AAA GTC ACC GTT GAG CAT CCG GAT AAA CTG GAA GAG AAA TTC       144
Gly Ile Lys Val Thr Val Glu His Pro Asp Lys Leu Glu Glu Lys Phe
            35                  40                  45

CCA CAG GTT GCG GCA ACT GGC GAT GGC CCT GAC ATT ATC TTC TGG GCA       192
Pro Gln Val Ala Ala Thr Gly Asp Gly Pro Asp Ile Ile Phe Trp Ala
        50                  55                  60

CAC GAC CGC TTT GGT GGC TAC GCT CAA TCT GGC CTG TTG GCT GAA ATC       240
His Asp Arg Phe Gly Gly Tyr Ala Gln Ser Gly Leu Leu Ala Glu Ile
 65                 70                  75                  80

ACC CCG GAC AAA GCG TTC CAG GAC AAG CTG TAT CCG TTT ACC TGG GAT       288
Thr Pro Asp Lys Ala Phe Gln Asp Lys Leu Tyr Pro Phe Thr Trp Asp
                85                  90                  95
```

```
GCC GTA CGT TAC AAC GGC AAG CTG ATT GCT TAC CCG ATC GCT GTT GAA      336
Ala Val Arg Tyr Asn Gly Lys Leu Ile Ala Tyr Pro Ile Ala Val Glu
            100                 105                 110

GCG TTA TCG CTG ATT TAT AAC AAA GAT CTG CTG CCG AAC CCG CCA AAA      384
Ala Leu Ser Leu Ile Tyr Asn Lys Asp Leu Leu Pro Asn Pro Pro Lys
                115                 120                 125

ACC TGG GAA GAG ATC CCG GCG CTG GAT AAA GAA CTG AAA GCG AAA GGT      432
Thr Trp Glu Glu Ile Pro Ala Leu Asp Lys Glu Leu Lys Ala Lys Gly
        130                 135                 140

AAG AGC GCG CTG ATG TTC AAC CTG CAA GAA CCG TAC TTC ACC TGG CCG      480
Lys Ser Ala Leu Met Phe Asn Leu Gln Glu Pro Tyr Phe Thr Trp Pro
145                 150                 155                 160

CTG ATT GCT GCT GAC GGG GGT TAT GCG TTC AAG TAT GAA AAC GGC AAG      528
Leu Ile Ala Ala Asp Gly Gly Tyr Ala Phe Lys Tyr Glu Asn Gly Lys
                165                 170                 175

TAC GAC ATT AAA GAC GTG GGC GTG GAT AAC GCT GGC GCG AAA GCG GGT      576
Tyr Asp Ile Lys Asp Val Gly Val Asp Asn Ala Gly Ala Lys Ala Gly
                180                 185                 190

CTG ACC TTC CTG GTT GAC CTG ATT AAA AAC AAA CAC ATG AAT GCA GAC      624
Leu Thr Phe Leu Val Asp Leu Ile Lys Asn Lys His Met Asn Ala Asp
        195                 200                 205

ACC GAT TAC TCC ATC GCA GAA GCT GCC TTT AAT AAA GGC GAA ACA GCG      672
Thr Asp Tyr Ser Ile Ala Glu Ala Ala Phe Asn Lys Gly Glu Thr Ala
        210                 215                 220

ATG ACC ATC AAC GGC CCG TGG GCA TGG TCC AAC ATC GAC ACC AGC AAA      720
Met Thr Ile Asn Gly Pro Trp Ala Trp Ser Asn Ile Asp Thr Ser Lys
225                 230                 235                 240

GTG AAT TAT GGT GTA ACG GTA CTG CCG ACC TTC AAG GGT CAA CCA TCC      768
Val Asn Tyr Gly Val Thr Val Leu Pro Thr Phe Lys Gly Gln Pro Ser
                245                 250                 255

AAA CCG TTC GTT GGC GTG CTG AGC GCA GGT ATT AAC GCC GCC AGT CCG      816
Lys Pro Phe Val Gly Val Leu Ser Ala Gly Ile Asn Ala Ala Ser Pro
                260                 265                 270

AAC AAA GAG CTG GCG AAA GAG TTC CTC GAA AAC TAT CTG CTG ACT GAT      864
Asn Lys Glu Leu Ala Lys Glu Phe Leu Glu Asn Tyr Leu Leu Thr Asp
        275                 280                 285

GAA GGT CTG GAA GCG GTT AAT AAA GAC AAA CCG CTG GGT GCC GTA GCG      912
Glu Gly Leu Glu Ala Val Asn Lys Asp Lys Pro Leu Gly Ala Val Ala
        290                 295                 300

CTG AAG TCT TAC GAG GAA GAG TTG GCG AAA GAT CCA CGT ATT GCC GCC      960
Leu Lys Ser Tyr Glu Glu Glu Leu Ala Lys Asp Pro Arg Ile Ala Ala
305                 310                 315                 320

ACC ATG GAA AAC GCC CAG AAA GGT GAA ATC ATG CCG AAC ATC CCG CAG     1008
Thr Met Glu Asn Ala Gln Lys Gly Glu Ile Met Pro Asn Ile Pro Gln
                325                 330                 335

ATG TCC GCT TTC TGG TAT GCC GTG CGT ACT GCG GTG ATC AAC GCC GCC     1056
Met Ser Ala Phe Trp Tyr Ala Val Arg Thr Ala Val Ile Asn Ala Ala
                340                 345                 350

AGC GGT CGT CAG ACT GTC GAT GAA GCC CTG AAA GAC GCG CAG ACT AAT     1104
Ser Gly Arg Gln Thr Val Asp Glu Ala Leu Lys Asp Ala Gln Thr Asn
        355                 360                 365

TCG AGC TCG GTA CCC GGC CGG GGA TCC ATC GAG GGT AGG ATT GCT GGA     1152
Ser Ser Ser Val Pro Gly Arg Gly Ser Ile Glu Gly Arg Ile Ala Gly
        370                 375                 380

CCT GAG TGG CTG CTA GAC CGT CCA TCT GTC AAC AAC AGC CAA TTA GTT     1200
Pro Glu Trp Leu Leu Asp Arg Pro Ser Val Asn Asn Ser Gln Leu Val
385                 390                 395                 400

GTT AGC GTT GCT GGT ACT GTT GAG GGG ACG AAT CAA GAC ATT AGT CTT     1248
Val Ser Val Ala Gly Thr Val Glu Gly Thr Asn Gln Asp Ile Ser Leu
                405                 410                 415
```

```
AAA TTT TTT GAA ATC GAT CTA ACA TCA CGA CCT GCT CAT GGA GGA AAG      1296
Lys Phe Phe Glu Ile Asp Leu Thr Ser Arg Pro Ala His Gly Gly Lys
            420                 425                 430

ACA GAG CAA GGC TTA AGT CCA AAA TCA AAA CCA TTT GCT ACT GAT AGT      1344
Thr Glu Gln Gly Leu Ser Pro Lys Ser Lys Pro Phe Ala Thr Asp Ser
        435                 440                 445

GGC GCG ATG TCA CAT AAA CTT GAG AAA GCT GAC TTA CTA AAG GCT ATT      1392
Gly Ala Met Ser His Lys Leu Glu Lys Ala Asp Leu Leu Lys Ala Ile
    450                 455                 460

CAA GAA CAA TTG ATC GCT AAC GTC CAC AGT AAC GAC GAC TAC TTT GAG      1440
Gln Glu Gln Leu Ile Ala Asn Val His Ser Asn Asp Asp Tyr Phe Glu
465                 470                 475                 480

GTC ATT GAT TTT GCA AGC GAT GCA ACC ATT ACT GAT CGA AAC GGC AAG      1488
Val Ile Asp Phe Ala Ser Asp Ala Thr Ile Thr Asp Arg Asn Gly Lys
                485                 490                 495

GTC TAC TTT GCT GAC AAA GAT GGT TCG GTA ACC TTG CCG ACC CAA CCT      1536
Val Tyr Phe Ala Asp Lys Asp Gly Ser Val Thr Leu Pro Thr Gln Pro
                500                 505                 510

GTC CAA GAA TTT TTG CTA AGC GGA CAT GTG CGC GTT AGA CCA TAT AAA      1584
Val Gln Glu Phe Leu Leu Ser Gly His Val Arg Val Arg Pro Tyr Lys
            515                 520                 525

GAA AAA CCA ATA CAA AAC CAA GCG AAA TCT GTT GAT GTG GAA TAT ACT      1632
Glu Lys Pro Ile Gln Asn Gln Ala Lys Ser Val Asp Val Glu Tyr Thr
        530                 535                 540

GTA CAG TTT ACT CCC TTA AAC CCT GAT GAC GAT TTC AGA CCA GGT CTC      1680
Val Gln Phe Thr Pro Leu Asn Pro Asp Asp Asp Phe Arg Pro Gly Leu
545                 550                 555                 560

AAA GAT ACT AAG CTA TTG AAA ACA CTA GCT ATC GGT GAC ACC ATC ACA      1728
Lys Asp Thr Lys Leu Leu Lys Thr Leu Ala Ile Gly Asp Thr Ile Thr
                565                 570                 575

TCT CAA GAA TTA CTA GCT CAA GCA CAA AGC ATT TTA AAC AAA AAC CAC      1776
Ser Gln Glu Leu Leu Ala Gln Ala Gln Ser Ile Leu Asn Lys Asn His
                580                 585                 590

CCA GGC TAT ACG ATT TAT GAA CGT GAC TCC TCA ATC GTC ACT CAT GAC      1824
Pro Gly Tyr Thr Ile Tyr Glu Arg Asp Ser Ser Ile Val Thr His Asp
            595                 600                 605

AAT GAC ATT TTC CGT ACG ATT TTA CCA ATG GAT CAA GAG TTT ACT TAC      1872
Asn Asp Ile Phe Arg Thr Ile Leu Pro Met Asp Gln Glu Phe Thr Tyr
610                 615                 620

CGT GTT AAA AAT CGG GAA CAA GCT TAT AGG ATC AAT AAA AAA TCT GGT      1920
Arg Val Lys Asn Arg Glu Gln Ala Tyr Arg Ile Asn Lys Lys Ser Gly
625                 630                 635                 640

CTG AAT GAA GAA ATA AAC AAC ACT GAC CTG ATC TCT GAG AAA TAT TAC      1968
Leu Asn Glu Glu Ile Asn Asn Thr Asp Leu Ile Ser Glu Lys Tyr Tyr
                645                 650                 655

GTC CTT AAA AAA GGG GAA AAG CCG TAT GAT CCC TTT GAT CGC AGT CAC      2016
Val Leu Lys Lys Gly Glu Lys Pro Tyr Asp Pro Phe Asp Arg Ser His
                660                 665                 670

TTG AAA CTG TTC ACC ATC AAA TAC GTT GAT GTC GAT ACC AAC GAA TTG      2064
Leu Lys Leu Phe Thr Ile Lys Tyr Val Asp Val Asp Thr Asn Glu Leu
            675                 680                 685

CTA AAA AGT GAG CAG CTC TTA ACA GCT AGC GAA CGT AAC TTA GAC TTC      2112
Leu Lys Ser Glu Gln Leu Leu Thr Ala Ser Glu Arg Asn Leu Asp Phe
        690                 695                 700

AGA GAT TTA TAC GAT CCT CGT GAT AAG GCT AAA CTA CTC TAC AAC AAT      2160
Arg Asp Leu Tyr Asp Pro Arg Asp Lys Ala Lys Leu Leu Tyr Asn Asn
705                 710                 715                 720

CTC GAT GCT TTT GGT ATT ATG GAC TAT ACC TTA ACT GGA AAA GTA GAG      2208
Leu Asp Ala Phe Gly Ile Met Asp Tyr Thr Leu Thr Gly Lys Val Glu
```

```
                          725                 730                 735
GAT AAT CAC GAT GAC ACC AAC CGT ATC ATA ACC GTT TAT ATG GGC AAG        2256
Asp Asn His Asp Asp Thr Asn Arg Ile Ile Thr Val Tyr Met Gly Lys
            740                 745                 750

CGA CCC GAA GGA GAG AAT GCT AGC TAT CAT TTA GCC TAT GAT AAA GAT        2304
Arg Pro Glu Gly Glu Asn Ala Ser Tyr His Leu Ala Tyr Asp Lys Asp
            755                 760                 765

CGT TAT ACC GAA GAA GAA CGA GAA GTT TAC AGC TAC CTG CGT TAT ACA        2352
Arg Tyr Thr Glu Glu Glu Arg Glu Val Tyr Ser Tyr Leu Arg Tyr Thr
    770                 775                 780

GGG ACA CCT ATA CCT GAT AAC CCT AAC GAC AAA                            2385
Gly Thr Pro Ile Pro Asp Asn Pro Asn Asp Lys
785                 790                 795

(2) INFORMATION FOR SEQ ID NO:2:

(i) SEQUENCE CHARACTERISTICS:
        (A) LENGTH: 795 amino acids
        (B) TYPE: amino acid
        (D) TOPOLOGY: linear (ii) MOLECULE TYPE: protein (xi) SEQUENCE DESCRIPTION: SEQ ID NO:2:

Met Lys Thr Glu Glu Gly Lys Leu Val Ile Trp Ile Asn Gly Asp Lys
1               5                   10                  15

Gly Tyr Asn Gly Leu Ala Glu Val Gly Lys Lys Phe Glu Lys Asp Thr
            20                  25                  30

Gly Ile Lys Val Thr Val Glu His Pro Asp Lys Leu Glu Glu Lys Phe
        35                  40                  45

Pro Gln Val Ala Ala Thr Gly Asp Gly Pro Asp Ile Ile Phe Trp Ala
    50                  55                  60

His Asp Arg Phe Gly Gly Tyr Ala Gln Ser Gly Leu Leu Ala Glu Ile
65                  70                  75                  80

Thr Pro Asp Lys Ala Phe Gln Asp Lys Leu Tyr Pro Phe Thr Trp Asp
                85                  90                  95

Ala Val Arg Tyr Asn Gly Lys Leu Ile Ala Tyr Pro Ile Ala Val Glu
            100                 105                 110

Ala Leu Ser Leu Ile Tyr Asn Lys Asp Leu Leu Pro Asn Pro Pro Lys
        115                 120                 125

Thr Trp Glu Glu Ile Pro Ala Leu Asp Lys Glu Leu Lys Ala Lys Gly
    130                 135                 140

Lys Ser Ala Leu Met Phe Asn Leu Gln Glu Pro Tyr Phe Thr Trp Pro
145                 150                 155                 160

Leu Ile Ala Ala Asp Gly Gly Tyr Ala Phe Lys Tyr Glu Asn Gly Lys
                165                 170                 175

Tyr Asp Ile Lys Asp Val Gly Val Asp Asn Ala Gly Ala Lys Ala Gly
            180                 185                 190

Leu Thr Phe Leu Val Asp Leu Ile Lys Asn Lys His Met Asn Ala Asp
        195                 200                 205

Thr Asp Tyr Ser Ile Ala Glu Ala Ala Phe Asn Lys Gly Glu Thr Ala
    210                 215                 220

Met Thr Ile Asn Gly Pro Trp Ala Trp Ser Asn Ile Asp Thr Ser Lys
225                 230                 235                 240

Val Asn Tyr Gly Val Thr Val Leu Pro Thr Phe Lys Gly Gln Pro Ser
                245                 250                 255

Lys Pro Phe Val Gly Val Leu Ser Ala Gly Ile Asn Ala Ala Ser Pro
```

-continued

```
                260                 265                 270
    Asn Lys Glu Leu Ala Lys Glu Phe Leu Glu Asn Tyr Leu Leu Thr Asp
                275                 280                 285

Glu Gly Leu Glu Ala Val Asn Lys Asp Lys Pro Leu Gly Ala Val Ala
                290                 295                 300

Leu Lys Ser Tyr Glu Glu Leu Ala Lys Asp Pro Arg Ile Ala Ala
    305                 310                 315                 320

Thr Met Glu Asn Ala Gln Lys Gly Glu Ile Met Pro Asn Ile Pro Gln
                    325                 330                 335

Met Ser Ala Phe Trp Tyr Ala Val Arg Thr Ala Val Ile Asn Ala Ala
                    340                 345                 350

Ser Gly Arg Gln Thr Val Asp Glu Ala Leu Lys Asp Ala Gln Thr Asn
                    355                 360                 365

Ser Ser Ser Val Pro Gly Arg Gly Ser Ile Glu Gly Arg Ile Ala Gly
                    370                 375                 380

Pro Glu Trp Leu Leu Asp Arg Pro Ser Val Asn Asn Ser Gln Leu Val
    385                 390                 395                 400

Val Ser Val Ala Gly Thr Val Glu Gly Thr Asn Gln Asp Ile Ser Leu
                    405                 410                 415

Lys Phe Phe Glu Ile Asp Leu Thr Ser Arg Pro Ala His Gly Gly Lys
                    420                 425                 430

Thr Glu Gln Gly Leu Ser Pro Lys Ser Lys Pro Phe Ala Thr Asp Ser
                    435                 440                 445

Gly Ala Met Ser His Lys Leu Glu Lys Ala Asp Leu Leu Lys Ala Ile
                    450                 455                 460

Gln Glu Gln Leu Ile Ala Asn Val His Ser Asn Asp Tyr Phe Glu
    465                 470                 475                 480

Val Ile Asp Phe Ala Ser Asp Ala Thr Ile Thr Asp Arg Asn Gly Lys
                    485                 490                 495

Val Tyr Phe Ala Asp Lys Asp Gly Ser Val Thr Leu Pro Thr Gln Pro
                    500                 505                 510

Val Gln Glu Phe Leu Leu Ser Gly His Val Arg Val Arg Pro Tyr Lys
                    515                 520                 525

Glu Lys Pro Ile Gln Asn Gln Ala Lys Ser Val Asp Val Glu Tyr Thr
                    530                 535                 540

Val Gln Phe Thr Pro Leu Asn Pro Asp Asp Phe Arg Pro Gly Leu
    545                 550                 555                 560

Lys Asp Thr Lys Leu Leu Lys Thr Leu Ala Ile Gly Asp Thr Ile Thr
                    565                 570                 575

Ser Gln Glu Leu Leu Ala Gln Ala Gln Ser Ile Leu Asn Lys Asn His
                    580                 585                 590

Pro Gly Tyr Thr Ile Tyr Glu Arg Asp Ser Ser Ile Val Thr His Asp
                    595                 600                 605

Asn Asp Ile Phe Arg Thr Ile Leu Pro Met Asp Gln Glu Phe Thr Tyr
    610                 615                 620

Arg Val Lys Asn Arg Glu Gln Ala Tyr Arg Ile Asn Lys Lys Ser Gly
    625                 630                 635                 640

Leu Asn Glu Glu Ile Asn Asn Thr Asp Leu Ile Ser Glu Lys Tyr Tyr
                    645                 650                 655

Val Leu Lys Lys Gly Glu Lys Pro Tyr Asp Pro Phe Asp Arg Ser His
                    660                 665                 670

Leu Lys Leu Phe Thr Ile Lys Tyr Val Asp Val Asp Thr Asn Glu Leu
                    675                 680                 685
```

```
Leu Lys Ser Glu Gln Leu Leu Thr Ala Ser Glu Arg Asn Leu Asp Phe
    690             695                 700
Arg Asp Leu Tyr Asp Pro Arg Asp Lys Ala Lys Leu Leu Tyr Asn Asn
705             710                 715                 720
Leu Asp Ala Phe Gly Ile Met Asp Tyr Thr Leu Thr Gly Lys Val Glu
                725                 730                 735
Asp Asn His Asp Asp Thr Asn Arg Ile Ile Thr Val Tyr Met Gly Lys
            740                 745                 750
Arg Pro Glu Gly Glu Asn Ala Ser Tyr His Leu Ala Tyr Asp Lys Asp
        755                 760                 765
Arg Tyr Thr Glu Glu Glu Arg Glu Val Tyr Ser Tyr Leu Arg Tyr Thr
    770                 775                 780
Gly Thr Pro Ile Pro Asp Asn Pro Asn Asp Lys
785             790                 795

(2) INFORMATION FOR SEQ ID NO:3:

(i) SEQUENCE CHARACTERISTICS:
        (A) LENGTH: 2208 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..2208

(xi) SEQUENCE DESCRIPTION: SEQ ID NO:3:

ATG AAA ACT GAA GAA GGT AAA CTG GTA ATC TGG ATT AAC GGC GAT AAA      48
Met Lys Thr Glu Glu Gly Lys Leu Val Ile Trp Ile Asn Gly Asp Lys
 1               5                  10                  15

GGC TAT AAC GGT CTC GCT GAA GTC GGT AAG AAA TTC GAG AAA GAT ACC      96
Gly Tyr Asn Gly Leu Ala Glu Val Gly Lys Lys Phe Glu Lys Asp Thr
                20                  25                  30

GGA ATT AAA GTC ACC GTT GAG CAT CCG GAT AAA CTG GAA GAG AAA TTC     144
Gly Ile Lys Val Thr Val Glu His Pro Asp Lys Leu Glu Glu Lys Phe
            35                  40                  45

CCA CAG GTT GCG GCA ACT GGC GAT GGC CCT GAC ATT ATC TTC TGG GCA     192
Pro Gln Val Ala Ala Thr Gly Asp Gly Pro Asp Ile Ile Phe Trp Ala
        50                  55                  60

CAC GAC CGC TTT GGT GGC TAC GCT CAA TCT GGC CTG TTG GCT GAA ATC     240
His Asp Arg Phe Gly Gly Tyr Ala Gln Ser Gly Leu Leu Ala Glu Ile
 65                 70                  75                  80

ACC CCG GAC AAA GCG TTC CAG GAC AAG CTG TAT CCG TTT ACC TGG GAT     288
Thr Pro Asp Lys Ala Phe Gln Asp Lys Leu Tyr Pro Phe Thr Trp Asp
                 85                  90                  95

GCC GTA CGT TAC AAC GGC AAG CTG ATT GCT TAC CCG ATC GCT GTT GAA     336
Ala Val Arg Tyr Asn Gly Lys Leu Ile Ala Tyr Pro Ile Ala Val Glu
                100                 105                 110

GCG TTA TCG CTG ATT TAT AAC AAA GAT CTG CTG CCG AAC CCG CCA AAA     384
Ala Leu Ser Leu Ile Tyr Asn Lys Asp Leu Leu Pro Asn Pro Pro Lys
            115                 120                 125

ACC TGG GAA GAG ATC CCG GCG CTG GAT AAA GAA CTG AAA GCG AAA GGT     432
Thr Trp Glu Glu Ile Pro Ala Leu Asp Lys Glu Leu Lys Ala Lys Gly
        130                 135                 140

AAG AGC GCG CTG ATG TTC AAC CTG CAA GAA CCG TAC TTC ACC TGG CCG     480
Lys Ser Ala Leu Met Phe Asn Leu Gln Glu Pro Tyr Phe Thr Trp Pro
145                 150                 155                 160
```

```
CTG ATT GCT GCT GAC GGG GGT TAT GCG TTC AAG TAT GAA AAC GGC AAG      528
Leu Ile Ala Ala Asp Gly Gly Tyr Ala Phe Lys Tyr Glu Asn Gly Lys
            165                 170                 175

TAC GAC ATT AAA GAC GTG GGC GTG GAT AAC GCT GGC GCG AAA GCG GGT      576
Tyr Asp Ile Lys Asp Val Gly Val Asp Asn Ala Gly Ala Lys Ala Gly
            180                 185                 190

CTG ACC TTC CTG GTT GAC CTG ATT AAA AAC AAA CAC ATG AAT GCA GAC      624
Leu Thr Phe Leu Val Asp Leu Ile Lys Asn Lys His Met Asn Ala Asp
            195                 200                 205

ACC GAT TAC TCC ATC GCA GAA GCT GCC TTT AAT AAA GGC GAA ACA GCG      672
Thr Asp Tyr Ser Ile Ala Glu Ala Ala Phe Asn Lys Gly Glu Thr Ala
            210                 215                 220

ATG ACC ATC AAC GGC CCG TGG GCA TGG TCC AAC ATC GAC ACC AGC AAA      720
Met Thr Ile Asn Gly Pro Trp Ala Trp Ser Asn Ile Asp Thr Ser Lys
225                 230                 235                 240

GTG AAT TAT GGT GTA ACG GTA CTG CCG ACC TTC AAG GGT CAA CCA TCC      768
Val Asn Tyr Gly Val Thr Val Leu Pro Thr Phe Lys Gly Gln Pro Ser
            245                 250                 255

AAA CCG TTC GTT GGC GTG CTG AGC GCA GGT ATT AAC GCC GCC AGT CCG      816
Lys Pro Phe Val Gly Val Leu Ser Ala Gly Ile Asn Ala Ala Ser Pro
            260                 265                 270

AAC AAA GAG CTG GCG AAA GAG TTC CTC GAA AAC TAT CTG CTG ACT GAT      864
Asn Lys Glu Leu Ala Lys Glu Phe Leu Glu Asn Tyr Leu Leu Thr Asp
            275                 280                 285

GAA GGT CTG GAA GCG GTT AAT AAA GAC AAA CCG CTG GGT GCC GTA GCG      912
Glu Gly Leu Glu Ala Val Asn Lys Asp Lys Pro Leu Gly Ala Val Ala
            290                 295                 300

CTG AAG TCT TAC GAG GAA GAG TTG GCG AAA GAT CCA CGT ATT GCC GCC      960
Leu Lys Ser Tyr Glu Glu Glu Leu Ala Lys Asp Pro Arg Ile Ala Ala
305                 310                 315                 320

ACC ATG GAA AAC GCC CAG AAA GGT GAA ATC ATG CCG AAC ATC CCG CAG     1008
Thr Met Glu Asn Ala Gln Lys Gly Glu Ile Met Pro Asn Ile Pro Gln
            325                 330                 335

ATG TCC GCT TTC TGG TAT GCC GTG CGT ACT GCG GTG ATC AAC GCC GCC     1056
Met Ser Ala Phe Trp Tyr Ala Val Arg Thr Ala Val Ile Asn Ala Ala
            340                 345                 350

AGC GGT CGT CAG ACT GTC GAT GAA GCC CTG AAA GAC GCG CAG ACT AAT     1104
Ser Gly Arg Gln Thr Val Asp Glu Ala Leu Lys Asp Ala Gln Thr Asn
            355                 360                 365

TCG AGC TCG GTA CCC GGC CGG GGA TCC ATC GAG GGT AGG TCA AAA CCA     1152
Ser Ser Ser Val Pro Gly Arg Gly Ser Ile Glu Gly Arg Ser Lys Pro
            370                 375                 380

TTT GCT ACT GAT AGT GGC GCG ATG TCA CAT AAA CTT GAG AAA GCT GAC     1200
Phe Ala Thr Asp Ser Gly Ala Met Ser His Lys Leu Glu Lys Ala Asp
385                 390                 395                 400

TTA CTA AAG GCT ATT CAA GAA CAA TTG ATC GCT AAC GTC CAC AGT AAC     1248
Leu Leu Lys Ala Ile Gln Glu Gln Leu Ile Ala Asn Val His Ser Asn
            405                 410                 415

GAC GAC TAC TTT GAG GTC ATT GAT TTT GCA AGC GAT GCA ACC ATT ACT     1296
Asp Asp Tyr Phe Glu Val Ile Asp Phe Ala Ser Asp Ala Thr Ile Thr
            420                 425                 430

GAT CGA AAC GGC AAG GTC TAC TTT GCT GAC AAA GAT GGT TCG GTA ACC     1344
Asp Arg Asn Gly Lys Val Tyr Phe Ala Asp Lys Asp Gly Ser Val Thr
            435                 440                 445

TTG CCG ACC CAA CCT GTC CAA GAA TTT TTG CTA AGC GGA CAT GTG CGC     1392
Leu Pro Thr Gln Pro Val Gln Glu Phe Leu Leu Ser Gly His Val Arg
            450                 455                 460

GTT AGA CCA TAT AAA GAA AAA CCA ATA CAA AAC CAA GCG AAA TCT GTT     1440
Val Arg Pro Tyr Lys Glu Lys Pro Ile Gln Asn Gln Ala Lys Ser Val
465                 470                 475                 480
```

-continued

```
GAT GTG GAA TAT ACT GTA CAG TTT ACT CCC TTA AAC CCT GAT GAC GAT      1488
Asp Val Glu Tyr Thr Val Gln Phe Thr Pro Leu Asn Pro Asp Asp Asp
                    485                 490                 495

TTC AGA CCA GGT CTC AAA GAT ACT AAG CTA TTG AAA ACA CTA GCT ATC      1536
Phe Arg Pro Gly Leu Lys Asp Thr Lys Leu Leu Lys Thr Leu Ala Ile
                500                 505                 510

GGT GAC ACC ATC ACA TCT CAA GAA TTA CTA GCT CAA GCA CAA AGC ATT      1584
Gly Asp Thr Ile Thr Ser Gln Glu Leu Leu Ala Gln Ala Gln Ser Ile
                515                 520                 525

TTA AAC AAA AAC CAC CCA GGC TAT ACG ATT TAT GAA CGT GAC TCC TCA      1632
Leu Asn Lys Asn His Pro Gly Tyr Thr Ile Tyr Glu Arg Asp Ser Ser
            530                 535                 540

ATC GTC ACT CAT GAC AAT GAC ATT TTC CGT ACG ATT TTA CCA ATG GAT      1680
Ile Val Thr His Asp Asn Asp Ile Phe Arg Thr Ile Leu Pro Met Asp
545                 550                 555                 560

CAA GAG TTT ACT TAC CGT GTT AAA AAT CGG GAA CAA GCT TAT AGG ATC      1728
Gln Glu Phe Thr Tyr Arg Val Lys Asn Arg Glu Gln Ala Tyr Arg Ile
                565                 570                 575

AAT AAA AAA TCT GGT CTG AAT GAA GAA ATA AAC AAC ACT GAC CTG ATC      1776
Asn Lys Lys Ser Gly Leu Asn Glu Glu Ile Asn Asn Thr Asp Leu Ile
                580                 585                 590

TCT GAG AAA TAT TAC GTC CTT AAA AAA GGG GAA AAG CCG TAT GAT CCC      1824
Ser Glu Lys Tyr Tyr Val Leu Lys Lys Gly Glu Lys Pro Tyr Asp Pro
                595                 600                 605

TTT GAT CGC AGT CAC TTG AAA CTG TTC ACC ATC AAA TAC GTT GAT GTC      1872
Phe Asp Arg Ser His Leu Lys Leu Phe Thr Ile Lys Tyr Val Asp Val
            610                 615                 620

GAT ACC AAC GAA TTG CTA AAA AGT GAG CAG CTC TTA ACA GCT AGC GAA      1920
Asp Thr Asn Glu Leu Leu Lys Ser Glu Gln Leu Leu Thr Ala Ser Glu
625                 630                 635                 640

CGT AAC TTA GAC TTC AGA GAT TTA TAC GAT CCT CGT GAT AAG GCT AAA      1968
Arg Asn Leu Asp Phe Arg Asp Leu Tyr Asp Pro Arg Asp Lys Ala Lys
                645                 650                 655

CTA CTC TAC AAC AAT CTC GAT GCT TTT GGT ATT ATG GAC TAT ACC TTA      2016
Leu Leu Tyr Asn Asn Leu Asp Ala Phe Gly Ile Met Asp Tyr Thr Leu
                660                 665                 670

ACT GGA AAA GTA GAG GAT AAT CAC GAT GAC ACC AAC CGT ATC ATA ACC      2064
Thr Gly Lys Val Glu Asp Asn His Asp Asp Thr Asn Arg Ile Ile Thr
                675                 680                 685

GTT TAT ATG GGC AAG CGA CCC GAA GGA GAG AAT GCT AGC TAT CAT TTA      2112
Val Tyr Met Gly Lys Arg Pro Glu Gly Glu Asn Ala Ser Tyr His Leu
690                 695                 700

GCC TAT GAT AAA GAT CGT TAT ACC GAA GAA GAA CGA GAA GTT TAC AGC      2160
Ala Tyr Asp Lys Asp Arg Tyr Thr Glu Glu Glu Arg Glu Val Tyr Ser
705                 710                 715                 720

TAC CTG CGT TAT ACA GGG ACA CCT ATA CCT GAT AAC CCT AAC GAC AAA      2208
Tyr Leu Arg Tyr Thr Gly Thr Pro Ile Pro Asp Asn Pro Asn Asp Lys
                725                 730                 735

(2) INFORMATION FOR SEQ ID NO:4:

(i) SEQUENCE CHARACTERISTICS:
        (A) LENGTH: 736 amino acids
        (B) TYPE: amino acid
        (D) TOPOLOGY: linear (ii) MOLECULE TYPE: protein (xi) SEQUENCE DESCRIPTION: SEQ ID NO:4:

Met Lys Thr Glu Glu Gly Lys Leu Val Ile Trp Ile Asn Gly Asp Lys
 1               5                  10                  15
```

```
Gly Tyr Asn Gly Leu Ala Glu Val Gly Lys Lys Phe Glu Lys Asp Thr
                 20                  25                  30

Gly Ile Lys Val Thr Val Glu His Pro Asp Lys Leu Glu Glu Lys Phe
             35                  40                  45

Pro Gln Val Ala Ala Thr Gly Asp Gly Pro Asp Ile Ile Phe Trp Ala
         50                  55                  60

His Asp Arg Phe Gly Gly Tyr Ala Gln Ser Gly Leu Leu Ala Glu Ile
 65                  70                  75                  80

Thr Pro Asp Lys Ala Phe Gln Asp Lys Leu Tyr Pro Phe Thr Trp Asp
                 85                  90                  95

Ala Val Arg Tyr Asn Gly Lys Leu Ile Ala Tyr Pro Ile Ala Val Glu
            100                 105                 110

Ala Leu Ser Leu Ile Tyr Asn Lys Asp Leu Leu Pro Asn Pro Pro Lys
            115                 120                 125

Thr Trp Glu Glu Ile Pro Ala Leu Asp Lys Glu Leu Lys Ala Lys Gly
            130                 135                 140

Lys Ser Ala Leu Met Phe Asn Leu Gln Glu Pro Tyr Phe Thr Trp Pro
145                 150                 155                 160

Leu Ile Ala Ala Asp Gly Gly Tyr Ala Phe Lys Tyr Glu Asn Gly Lys
                165                 170                 175

Tyr Asp Ile Lys Asp Val Gly Val Asp Asn Ala Gly Ala Lys Ala Gly
                180                 185                 190

Leu Thr Phe Leu Val Asp Leu Ile Lys Asn Lys His Met Asn Ala Asp
            195                 200                 205

Thr Asp Tyr Ser Ile Ala Glu Ala Ala Phe Asn Lys Gly Glu Thr Ala
            210                 215                 220

Met Thr Ile Asn Gly Pro Trp Ala Trp Ser Asn Ile Asp Thr Ser Lys
225                 230                 235                 240

Val Asn Tyr Gly Val Thr Val Leu Pro Thr Phe Lys Gly Gln Pro Ser
                245                 250                 255

Lys Pro Phe Val Gly Val Leu Ser Ala Gly Ile Asn Ala Ala Ser Pro
                260                 265                 270

Asn Lys Glu Leu Ala Lys Glu Phe Leu Glu Asn Tyr Leu Leu Thr Asp
            275                 280                 285

Glu Gly Leu Glu Ala Val Asn Lys Asp Lys Pro Leu Gly Ala Val Ala
            290                 295                 300

Leu Lys Ser Tyr Glu Glu Glu Leu Ala Lys Asp Pro Arg Ile Ala Ala
305                 310                 315                 320

Thr Met Glu Asn Ala Gln Lys Gly Glu Ile Met Pro Asn Ile Pro Gln
            325                 330                 335

Met Ser Ala Phe Trp Tyr Ala Val Arg Thr Ala Val Ile Asn Ala Ala
                340                 345                 350

Ser Gly Arg Gln Thr Val Asp Glu Ala Leu Lys Asp Ala Gln Thr Asn
            355                 360                 365

Ser Ser Ser Val Pro Gly Arg Gly Ser Ile Glu Gly Arg Ser Lys Pro
            370                 375                 380

Phe Ala Thr Asp Ser Gly Ala Met Ser His Lys Leu Glu Lys Ala Asp
385                 390                 395                 400

Leu Leu Lys Ala Ile Gln Glu Gln Leu Ile Ala Asn Val His Ser Asn
                405                 410                 415

Asp Asp Tyr Phe Glu Val Ile Asp Phe Ala Ser Asp Ala Thr Ile Thr
                420                 425                 430
```

```
Asp Arg Asn Gly Lys Val Tyr Phe Ala Asp Lys Asp Gly Ser Val Thr
        435                 440                 445

Leu Pro Thr Gln Pro Val Gln Glu Phe Leu Leu Ser Gly His Val Arg
    450                 455                 460

Val Arg Pro Tyr Lys Glu Lys Pro Ile Gln Asn Gln Ala Lys Ser Val
465                 470                 475                 480

Asp Val Glu Tyr Thr Val Gln Phe Thr Pro Leu Asn Pro Asp Asp Asp
                485                 490                 495

Phe Arg Pro Gly Leu Lys Asp Thr Lys Leu Leu Lys Thr Leu Ala Ile
            500                 505                 510

Gly Asp Thr Ile Thr Ser Gln Glu Leu Leu Ala Gln Ala Gln Ser Ile
        515                 520                 525

Leu Asn Lys Asn His Pro Gly Tyr Thr Ile Tyr Glu Arg Asp Ser Ser
    530                 535                 540

Ile Val Thr His Asp Asn Asp Ile Phe Arg Thr Ile Leu Pro Met Asp
545                 550                 555                 560

Gln Glu Phe Thr Tyr Arg Val Lys Asn Arg Glu Gln Ala Tyr Arg Ile
                565                 570                 575

Asn Lys Lys Ser Gly Leu Asn Glu Glu Ile Asn Asn Thr Asp Leu Ile
            580                 585                 590

Ser Glu Lys Tyr Tyr Val Leu Lys Lys Gly Glu Lys Pro Tyr Asp Pro
        595                 600                 605

Phe Asp Arg Ser His Leu Lys Leu Phe Thr Ile Lys Tyr Val Asp Val
    610                 615                 620

Asp Thr Asn Glu Leu Leu Lys Ser Glu Gln Leu Leu Thr Ala Ser Glu
625                 630                 635                 640

Arg Asn Leu Asp Phe Arg Asp Leu Tyr Asp Pro Arg Asp Lys Ala Lys
                645                 650                 655

Leu Leu Tyr Asn Asn Leu Asp Ala Phe Gly Ile Met Asp Tyr Thr Leu
            660                 665                 670

Thr Gly Lys Val Glu Asp Asn His Asp Asp Thr Asn Arg Ile Ile Thr
        675                 680                 685

Val Tyr Met Gly Lys Arg Pro Glu Gly Glu Asn Ala Ser Tyr His Leu
    690                 695                 700

Ala Tyr Asp Lys Asp Arg Tyr Thr Glu Glu Arg Glu Val Tyr Ser
705                 710                 715                 720

Tyr Leu Arg Tyr Thr Gly Thr Pro Ile Pro Asp Asn Pro Asn Asp Lys
                725                 730                 735
```

(2) INFORMATION FOR SEQ ID NO:5:

(i) SEQUENCE CHARACTERISTICS:
        (A) LENGTH: 1242 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..1242

(xi) SEQUENCE DESCRIPTION: SEQ ID NO:5:

```
ATT GCT GGA CCT GAG TGG CTG CTA GAC CGT CCA TCT GTC AAC AAC AGC      48
Ile Ala Gly Pro Glu Trp Leu Leu Asp Arg Pro Ser Val Asn Asn Ser
  1               5                  10                  15

CAA TTA GTT GTT AGC GTT GCT GGT ACT GTT GAG GGG ACG AAT CAA GAC      96
```

```
Gln Leu Val Val Ser Val Ala Gly Thr Val Glu Gly Thr Asn Gln Asp
             20                  25                  30

ATT AGT CTT AAA TTT TTT GAA ATC GAT CTA ACA TCA CGA CCT GCT CAT        144
Ile Ser Leu Lys Phe Phe Glu Ile Asp Leu Thr Ser Arg Pro Ala His
         35                  40                  45

GGA GGA AAG ACA GAG CAA GGC TTA AGT CCA AAA TCA AAA CCA TTT GCT        192
Gly Gly Lys Thr Glu Gln Gly Leu Ser Pro Lys Ser Lys Pro Phe Ala
 50                  55                  60

ACT GAT AGT GGC GCG ATG TCA CAT AAA CTT GAG AAA GCT GAC TTA CTA        240
Thr Asp Ser Gly Ala Met Ser His Lys Leu Glu Lys Ala Asp Leu Leu
 65                  70                  75                  80

AAG GCT ATT CAA GAA CAA TTG ATC GCT AAC GTC CAC AGT AAC GAC GAC        288
Lys Ala Ile Gln Glu Gln Leu Ile Ala Asn Val His Ser Asn Asp Asp
                 85                  90                  95

TAC TTT GAG GTC ATT GAT TTT GCA AGC GAT GCA ACC ATT ACT GAT CGA        336
Tyr Phe Glu Val Ile Asp Phe Ala Ser Asp Ala Thr Ile Thr Asp Arg
                100                 105                 110

AAC GGC AAG GTC TAC TTT GCT GAC AAA GAT GGT TCG GTA ACC TTG CCG        384
Asn Gly Lys Val Tyr Phe Ala Asp Lys Asp Gly Ser Val Thr Leu Pro
            115                 120                 125

ACC CAA CCT GTC CAA GAA TTT TTG CTA AGC GGA CAT GTG CGC GTT AGA        432
Thr Gln Pro Val Gln Glu Phe Leu Leu Ser Gly His Val Arg Val Arg
130                 135                 140

CCA TAT AAA GAA AAA CCA ATA CAA AAC CAA GCG AAA TCT GTT GAT GTG        480
Pro Tyr Lys Glu Lys Pro Ile Gln Asn Gln Ala Lys Ser Val Asp Val
145                 150                 155                 160

GAA TAT ACT GTA CAG TTT ACT CCC TTA AAC CCT GAT GAC GAT TTC AGA        528
Glu Tyr Thr Val Gln Phe Thr Pro Leu Asn Pro Asp Asp Asp Phe Arg
                165                 170                 175

CCA GGT CTC AAA GAT ACT AAG CTA TTG AAA ACA CTA GCT ATC GGT GAC        576
Pro Gly Leu Lys Asp Thr Lys Leu Leu Lys Thr Leu Ala Ile Gly Asp
            180                 185                 190

ACC ATC ACA TCT CAA GAA TTA CTA GCT CAA GCA CAA AGC ATT TTA AAC        624
Thr Ile Thr Ser Gln Glu Leu Leu Ala Gln Ala Gln Ser Ile Leu Asn
            195                 200                 205

AAA AAC CAC CCA GGC TAT ACG ATT TAT GAA CGT GAC TCC TCA ATC GTC        672
Lys Asn His Pro Gly Tyr Thr Ile Tyr Glu Arg Asp Ser Ser Ile Val
        210                 215                 220

ACT CAT GAC AAT GAC ATT TTC CGT ACG ATT TTA CCA ATG GAT CAA GAG        720
Thr His Asp Asn Asp Ile Phe Arg Thr Ile Leu Pro Met Asp Gln Glu
225                 230                 235                 240

TTT ACT TAC CGT GTT AAA AAT CGG GAA CAA GCT TAT AGG ATC AAT AAA        768
Phe Thr Tyr Arg Val Lys Asn Arg Glu Gln Ala Tyr Arg Ile Asn Lys
                245                 250                 255

AAA TCT GGT CTG AAT GAA GAA ATA AAC AAC ACT GAC CTG ATC TCT GAG        816
Lys Ser Gly Leu Asn Glu Glu Ile Asn Asn Thr Asp Leu Ile Ser Glu
            260                 265                 270

AAA TAT TAC GTC CTT AAA AAA GGG GAA AAG CCG TAT GAT CCC TTT GAT        864
Lys Tyr Tyr Val Leu Lys Lys Gly Glu Lys Pro Tyr Asp Pro Phe Asp
            275                 280                 285

CGC AGT CAC TTG AAA CTG TTC ACC ATC AAA TAC GTT GAT GTC GAT ACC        912
Arg Ser His Leu Lys Leu Phe Thr Ile Lys Tyr Val Asp Val Asp Thr
        290                 295                 300

AAC GAA TTG CTA AAA AGT GAG CAG CTC TTA ACA GCT AGC GAA CGT AAC        960
Asn Glu Leu Leu Lys Ser Glu Gln Leu Leu Thr Ala Ser Glu Arg Asn
305                 310                 315                 320

TTA GAC TTC AGA GAT TTA TAC GAT CCT CGT GAT AAG GCT AAA CTA CTC       1008
Leu Asp Phe Arg Asp Leu Tyr Asp Pro Arg Asp Lys Ala Lys Leu Leu
                325                 330                 335
```

```
TAC AAC AAT CTC GAT GCT TTT GGT ATT ATG GAC TAT ACC TTA ACT GGA        1056
Tyr Asn Asn Leu Asp Ala Phe Gly Ile Met Asp Tyr Thr Leu Thr Gly
                340                 345                 350

AAA GTA GAG GAT AAT CAC GAT GAC ACC AAC CGT ATC ATA ACC GTT TAT        1104
Lys Val Glu Asp Asn His Asp Asp Thr Asn Arg Ile Ile Thr Val Tyr
            355                 360                 365

ATG GGC AAG CGA CCC GAA GGA GAG AAT GCT AGC TAT CAT TTA GCC TAT        1152
Met Gly Lys Arg Pro Glu Gly Glu Asn Ala Ser Tyr His Leu Ala Tyr
        370                 375                 380

GAT AAA GAT CGT TAT ACC GAA GAA GAA CGA GAA GTT TAC AGC TAC CTG        1200
Asp Lys Asp Arg Tyr Thr Glu Glu Glu Arg Glu Val Tyr Ser Tyr Leu
385                 390                 395                 400

CGT TAT ACA GGG ACA CCT ATA CCT GAT AAC CCT AAC GAC AAA                1242
Arg Tyr Thr Gly Thr Pro Ile Pro Asp Asn Pro Asn Asp Lys
                405                 410
```

(2) INFORMATION FOR SEQ ID NO:6:

(i) SEQUENCE CHARACTERISTICS:
        (A) LENGTH: 414 amino acids
        (B) TYPE: amino acid
        (D) TOPOLOGY: linear (ii) MOLECULE TYPE: protein (xi) SEQUENCE DESCRIPTION: SEQ ID NO:6:

```
Ile Ala Gly Pro Glu Trp Leu Leu Asp Arg Pro Ser Val Asn Asn Ser
 1               5                  10                  15

Gln Leu Val Val Ser Val Ala Gly Thr Val Glu Gly Thr Asn Gln Asp
                20                  25                  30

Ile Ser Leu Lys Phe Phe Glu Ile Asp Leu Thr Ser Arg Pro Ala His
            35                  40                  45

Gly Gly Lys Thr Glu Gln Gly Leu Ser Pro Lys Ser Lys Pro Phe Ala
        50                  55                  60

Thr Asp Ser Gly Ala Met Ser His Lys Leu Glu Lys Ala Asp Leu Leu
65                  70                  75                  80

Lys Ala Ile Gln Glu Gln Leu Ile Ala Asn Val His Ser Asn Asp Asp
                85                  90                  95

Tyr Phe Glu Val Ile Asp Phe Ala Ser Asp Ala Thr Ile Thr Asp Arg
            100                 105                 110

Asn Gly Lys Val Tyr Phe Ala Asp Lys Asp Gly Ser Val Thr Leu Pro
        115                 120                 125

Thr Gln Pro Val Gln Glu Phe Leu Leu Ser Gly His Val Arg Val Arg
130                 135                 140

Pro Tyr Lys Glu Lys Pro Ile Gln Asn Gln Ala Lys Ser Val Asp Val
145                 150                 155                 160

Glu Tyr Thr Val Gln Phe Thr Pro Leu Asn Pro Asp Asp Phe Arg
            165                 170                 175

Pro Gly Leu Lys Asp Thr Lys Leu Leu Lys Thr Leu Ala Ile Gly Asp
        180                 185                 190

Thr Ile Thr Ser Gln Glu Leu Leu Ala Gln Ala Gln Ser Ile Leu Asn
        195                 200                 205

Lys Asn His Pro Gly Tyr Thr Ile Tyr Glu Arg Asp Ser Ser Ile Val
210                 215                 220

Thr His Asp Asn Asp Ile Phe Arg Thr Ile Leu Pro Met Asp Gln Glu
225                 230                 235                 240

Phe Thr Tyr Arg Val Lys Asn Arg Glu Gln Ala Tyr Arg Ile Asn Lys
                245                 250                 255
```

```
Lys Ser Gly Leu Asn Glu Glu Ile Asn Asn Thr Asp Leu Ile Ser Glu
            260                 265                 270
Lys Tyr Tyr Val Leu Lys Lys Gly Glu Lys Pro Tyr Asp Pro Phe Asp
            275                 280                 285
Arg Ser His Leu Lys Leu Phe Thr Ile Lys Tyr Val Asp Val Asp Thr
        290                 295                 300
Asn Glu Leu Leu Lys Ser Glu Gln Leu Leu Thr Ala Ser Glu Arg Asn
305                 310                 315                 320
Leu Asp Phe Arg Asp Leu Tyr Asp Pro Arg Asp Lys Ala Lys Leu Leu
                325                 330                 335
Tyr Asn Asn Leu Asp Ala Phe Gly Ile Met Asp Tyr Thr Leu Thr Gly
            340                 345                 350
Lys Val Glu Asp Asn His Asp Asp Thr Asn Arg Ile Ile Thr Val Tyr
            355                 360                 365
Met Gly Lys Arg Pro Glu Gly Glu Asn Ala Ser Tyr His Leu Ala Tyr
        370                 375                 380
Asp Lys Asp Arg Tyr Thr Glu Glu Glu Arg Glu Val Tyr Ser Tyr Leu
385                 390                 395                 400
Arg Tyr Thr Gly Thr Pro Ile Pro Asp Asn Pro Asn Asp Lys
                405                 410
```

(2) INFORMATION FOR SEQ ID NO:7:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: PCR primer (xi) SEQUENCE DESCRIPTION: SEQ ID NO:7:

GCGATATCGC TGGACCTGAG TGG                                  23

(2) INFORMATION FOR SEQ ID NO:8:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: PCR primer (xi) SEQUENCE DESCRIPTION: SEQ ID NO:8:

GCCTGCAGTC ATTATTTGTC GTTAGG                             26

(2) INFORMATION FOR SEQ ID NO:9:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: PCR primer (xi) SEQUENCE DESCRIPTION: SEQ ID NO:9:

CCCAGATCTA TGAAAAATTA CTTATCTTTT GG                    32

(2) INFORMATION FOR SEQ ID NO:10:

(i) SEQUENCE CHARACTERISTICS:
    (A) LENGTH: 35 base pairs
    (B) TYPE: nucleic acid
    (C) STRANDEDNESS: single
    (D) TOPOLOGY: linear (ii) MOLECULE TYPE: PCR primer (xi) SEQUENCE DESCRIPTION: SEQ ID NO:10:

CCCGGATCCT CATTATTTGT CGTTAGGGTT ATCAG                                35

(2) INFORMATION FOR SEQ ID NO:11:

(i) SEQUENCE CHARACTERISTICS:
        (A) LENGTH: 1068 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..1068

(xi) SEQUENCE DESCRIPTION: SEQ ID NO:11:

| | | | | | | | | | | | | | | | | |
|---|---|---|---|---|---|---|---|---|---|---|---|---|---|---|---|---|
| AAA | TCA | AAA | CCA | TTT | GCT | ACT | GAT | AGT | GGC | GCG | ATG | TCA | CAT | AAA | CTT | 48 |
| Lys | Ser | Lys | Pro | Phe | Ala | Thr | Asp | Ser | Gly | Ala | Met | Ser | His | Lys | Leu | |
| 1 | | | | 5 | | | | | 10 | | | | | 15 | | |
| GAG | AAA | GCT | GAC | TTA | CTA | AAG | GCT | ATT | CAA | GAA | CAA | TTG | ATC | GCT | AAC | 96 |
| Glu | Lys | Ala | Asp | Leu | Leu | Lys | Ala | Ile | Gln | Glu | Gln | Leu | Ile | Ala | Asn | |
| | | | 20 | | | | | 25 | | | | | 30 | | | |
| GTC | CAC | AGT | AAC | GAC | GAC | TAC | TTT | GAG | GTC | ATT | GAT | TTT | GCA | AGC | GAT | 144 |
| Val | His | Ser | Asn | Asp | Asp | Tyr | Phe | Glu | Val | Ile | Asp | Phe | Ala | Ser | Asp | |
| | | 35 | | | | | 40 | | | | | 45 | | | | |
| GCA | ACC | ATT | ACT | GAT | CGA | AAC | GGC | AAG | GTC | TAC | TTT | GCT | GAC | AAA | GAT | 192 |
| Ala | Thr | Ile | Thr | Asp | Arg | Asn | Gly | Lys | Val | Tyr | Phe | Ala | Asp | Lys | Asp | |
| | 50 | | | | | 55 | | | | | 60 | | | | | |
| GGT | TCG | GTA | ACC | TTG | CCG | ACC | CAA | CCT | GTC | CAA | GAA | TTT | TTG | CTA | AGC | 240 |
| Gly | Ser | Val | Thr | Leu | Pro | Thr | Gln | Pro | Val | Gln | Glu | Phe | Leu | Leu | Ser | |
| 65 | | | | | 70 | | | | | 75 | | | | | 80 | |
| GGA | CAT | GTG | CGC | GTT | AGA | CCA | TAT | AAA | GAA | AAA | CCA | ATA | CAA | AAC | CAA | 288 |
| Gly | His | Val | Arg | Val | Arg | Pro | Tyr | Lys | Glu | Lys | Pro | Ile | Gln | Asn | Gln | |
| | | | | 85 | | | | | 90 | | | | | 95 | | |
| GCG | AAA | TCT | GTT | GAT | GTG | GAA | TAT | ACT | GTA | CAG | TTT | ACT | CCC | TTA | AAC | 336 |
| Ala | Lys | Ser | Val | Asp | Val | Glu | Tyr | Thr | Val | Gln | Phe | Thr | Pro | Leu | Asn | |
| | | | 100 | | | | | 105 | | | | | 110 | | | |
| CCT | GAT | GAC | GAT | TTC | AGA | CCA | GGT | CTC | AAA | GAT | ACT | AAG | CTA | TTG | AAA | 384 |
| Pro | Asp | Asp | Asp | Phe | Arg | Pro | Gly | Leu | Lys | Asp | Thr | Lys | Leu | Leu | Lys | |
| | | 115 | | | | | 120 | | | | | 125 | | | | |
| ACA | CTA | GCT | ATC | GGT | GAC | ACC | ATC | ACA | TCT | CAA | GAA | TTA | CTA | GCT | CAA | 432 |
| Thr | Leu | Ala | Ile | Gly | Asp | Thr | Ile | Thr | Ser | Gln | Glu | Leu | Leu | Ala | Gln | |
| | 130 | | | | | 135 | | | | | 140 | | | | | |
| GCA | CAA | AGC | ATT | TTA | AAC | AAA | AAC | CAC | CCA | GGC | TAT | ACG | ATT | TAT | GAA | 480 |
| Ala | Gln | Ser | Ile | Leu | Asn | Lys | Asn | His | Pro | Gly | Tyr | Thr | Ile | Tyr | Glu | |
| 145 | | | | | 150 | | | | | 155 | | | | | 160 | |
| CGT | GAC | TCC | TCA | ATC | GTC | ACT | CAT | GAC | AAT | GAC | ATT | TTC | CGT | ACG | ATT | 528 |
| Arg | Asp | Ser | Ser | Ile | Val | Thr | His | Asp | Asn | Asp | Ile | Phe | Arg | Thr | Ile | |
| | | | | 165 | | | | | 170 | | | | | 175 | | |
| TTA | CCA | ATG | GAT | CAA | GAG | TTT | ACT | TAC | CGT | GTT | AAA | AAT | CGG | GAA | CAA | 576 |
| Leu | Pro | Met | Asp | Gln | Glu | Phe | Thr | Tyr | Arg | Val | Lys | Asn | Arg | Glu | Gln | |
| | | | 180 | | | | | 185 | | | | | 190 | | | |
| GCT | TAT | AGG | ATC | AAT | AAA | AAA | TCT | GGT | CTG | AAT | GAA | GAA | ATA | AAC | AAC | 624 |
| Ala | Tyr | Arg | Ile | Asn | Lys | Lys | Ser | Gly | Leu | Asn | Glu | Glu | Ile | Asn | Asn | |

```
                195                 200                 205
ACT GAC CTG ATC TCT GAG AAA TAT TAC GTC CTT AAA AAA GGG GAA AAG         672
Thr Asp Leu Ile Ser Glu Lys Tyr Tyr Val Leu Lys Lys Gly Glu Lys
        210                 215                 220

CCG TAT GAT CCC TTT GAT CGC AGT CAC TTG AAA CTG TTC ACC ATC AAA         720
Pro Tyr Asp Pro Phe Asp Arg Ser His Leu Lys Leu Phe Thr Ile Lys
225                 230                 235                 240

TAC GTT GAT GTC GAT ACC AAC GAA TTG CTA AAA AGT GAG CAG CTC TTA         768
Tyr Val Asp Val Asp Thr Asn Glu Leu Leu Lys Ser Glu Gln Leu Leu
                245                 250                 255

ACA GCT AGC GAA CGT AAC TTA GAC TTC AGA GAT TTA TAC GAT CCT CGT         816
Thr Ala Ser Glu Arg Asn Leu Asp Phe Arg Asp Leu Tyr Asp Pro Arg
            260                 265                 270

GAT AAG GCT AAA CTA CTC TAC AAC AAT CTC GAT GCT TTT GGT ATT ATG         864
Asp Lys Ala Lys Leu Leu Tyr Asn Asn Leu Asp Ala Phe Gly Ile Met
        275                 280                 285

GAC TAT ACC TTA ACT GGA AAA GTA GAG GAT AAT CAC GAT GAC ACC AAC         912
Asp Tyr Thr Leu Thr Gly Lys Val Glu Asp Asn His Asp Asp Thr Asn
290                 295                 300

CGT ATC ATA ACC GTT TAT ATG GGC AAG CGA CCC GAA GGA GAG AAT GCT         960
Arg Ile Ile Thr Val Tyr Met Gly Lys Arg Pro Glu Gly Glu Asn Ala
305                 310                 315                 320

AGC TAT CAT TTA GCC TAT GAT AAA GAT CGT TAT ACC GAA GAA GAA CGA        1008
Ser Tyr His Leu Ala Tyr Asp Lys Asp Arg Tyr Thr Glu Glu Glu Arg
                325                 330                 335

GAA GTT TAC AGC TAC CTG CGT TAT ACA GGG ACA CCT ATA CCT GAT AAC        1056
Glu Val Tyr Ser Tyr Leu Arg Tyr Thr Gly Thr Pro Ile Pro Asp Asn
            340                 345                 350

CCT AAC GAC AAA                                                         1068
Pro Asn Asp Lys
        355

(2) INFORMATION FOR SEQ ID NO:12:

(i) SEQUENCE CHARACTERISTICS:
        (A) LENGTH: 356 amino acids
        (B) TYPE: amino acid
        (D) TOPOLOGY: linear (ii) MOLECULE TYPE: protein (xi) SEQUENCE DESCRIPTION: SEQ ID NO:12:

Lys Ser Lys Pro Phe Ala Thr Asp Ser Gly Ala Met Ser His Lys Leu
  1               5                  10                  15

Glu Lys Ala Asp Leu Leu Lys Ala Ile Gln Glu Gln Leu Ile Ala Asn
                20                  25                  30

Val His Ser Asn Asp Asp Tyr Phe Glu Val Ile Asp Phe Ala Ser Asp
            35                  40                  45

Ala Thr Ile Thr Asp Arg Asn Gly Lys Val Tyr Phe Ala Asp Lys Asp
        50                  55                  60

Gly Ser Val Thr Leu Pro Thr Gln Pro Val Gln Glu Phe Leu Leu Ser
 65                  70                  75                  80

Gly His Val Arg Val Arg Pro Tyr Lys Glu Lys Pro Ile Gln Asn Gln
                85                  90                  95

Ala Lys Ser Val Asp Val Glu Tyr Thr Val Gln Phe Thr Pro Leu Asn
            100                 105                 110

Pro Asp Asp Asp Phe Arg Pro Gly Leu Lys Asp Thr Lys Leu Leu Lys
        115                 120                 125

Thr Leu Ala Ile Gly Asp Thr Ile Thr Ser Gln Glu Leu Leu Ala Gln
```

-continued

```
                130                 135                 140
Ala Gln Ser Ile Leu Asn Lys Asn His Pro Gly Tyr Thr Ile Tyr Glu
145                 150                 155                 160

Arg Asp Ser Ser Ile Val Thr His Asp Asn Asp Ile Phe Arg Thr Ile
                165                 170                 175

Leu Pro Met Asp Gln Glu Phe Thr Tyr Arg Val Lys Asn Arg Glu Gln
            180                 185                 190

Ala Tyr Arg Ile Asn Lys Lys Ser Gly Leu Asn Glu Glu Ile Asn Asn
            195                 200                 205

Thr Asp Leu Ile Ser Glu Lys Tyr Tyr Val Leu Lys Lys Gly Glu Lys
            210                 215                 220

Pro Tyr Asp Pro Phe Asp Arg Ser His Leu Lys Leu Phe Thr Ile Lys
225                 230                 235                 240

Tyr Val Asp Val Asp Thr Asn Glu Leu Leu Lys Ser Glu Gln Leu Leu
                245                 250                 255

Thr Ala Ser Glu Arg Asn Leu Asp Phe Arg Asp Leu Tyr Asp Pro Arg
                260                 265                 270

Asp Lys Ala Lys Leu Leu Tyr Asn Asn Leu Asp Ala Phe Gly Ile Met
            275                 280                 285

Asp Tyr Thr Leu Thr Gly Lys Val Glu Asp Asn His Asp Asp Thr Asn
            290                 295                 300

Arg Ile Ile Thr Val Tyr Met Gly Lys Arg Pro Glu Gly Glu Asn Ala
305                 310                 315                 320

Ser Tyr His Leu Ala Tyr Asp Lys Asp Arg Tyr Thr Glu Glu Glu Arg
                325                 330                 335

Glu Val Tyr Ser Tyr Leu Arg Tyr Thr Gly Thr Pro Ile Pro Asp Asn
                340                 345                 350

Pro Asn Asp Lys
        355

(2) INFORMATION FOR SEQ ID NO:13:

(i) SEQUENCE CHARACTERISTICS:
        (A) LENGTH: 450 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..450

(xi) SEQUENCE DESCRIPTION: SEQ ID NO:13:

AGA CCA TAT AAA GAA AAA CCA ATA CAA AAC CAA GCG AAA TCT GTT GAT      48
Arg Pro Tyr Lys Glu Lys Pro Ile Gln Asn Gln Ala Lys Ser Val Asp
1               5                   10                  15

GTG GAA TAT ACT GTA CAG TTT ACT CCC TTA AAC CCT GAT GAC GAT TTC      96
Val Glu Tyr Thr Val Gln Phe Thr Pro Leu Asn Pro Asp Asp Asp Phe
                20                  25                  30

AGA CCA GGT CTC AAA GAT ACT AAG CTA TTG AAA ACA CTA GCT ATC GGT     144
Arg Pro Gly Leu Lys Asp Thr Lys Leu Leu Lys Thr Leu Ala Ile Gly
            35                  40                  45

GAC ACC ATC ACA TCT CAA GAA TTA CTA GCT CAA GCA CAA AGC ATT TTA     192
Asp Thr Ile Thr Ser Gln Glu Leu Leu Ala Gln Ala Gln Ser Ile Leu
    50                  55                  60

AAC AAA AAC CAC CCA GGC TAT ACG ATT TAT GAA CGT GAC TCC TCA ATC     240
Asn Lys Asn His Pro Gly Tyr Thr Ile Tyr Glu Arg Asp Ser Ser Ile
```

```
            65                   70                  75                  80
GTC ACT CAT GAC AAT GAC ATT TTC CGT ACG ATT TTA CCA ATG GAT CAA           288
Val Thr His Asp Asn Asp Ile Phe Arg Thr Ile Leu Pro Met Asp Gln
                85                  90                  95

GAG TTT ACT TAC CGT GTT AAA AAT CGG GAA CAA GCT TAT AGG ATC AAT           336
Glu Phe Thr Tyr Arg Val Lys Asn Arg Glu Gln Ala Tyr Arg Ile Asn
            100                 105                 110

AAA AAA TCT GGT CTG AAT GAA GAA ATA AAC AAC ACT GAC CTG ATC TCT          384
Lys Lys Ser Gly Leu Asn Glu Glu Ile Asn Asn Thr Asp Leu Ile Ser
        115                 120                 125

GAG AAA TAT TAC GTC CTT AAA AAA GGG GAA AAG CCG TAT GAT CCC TTT          432
Glu Lys Tyr Tyr Val Leu Lys Lys Gly Glu Lys Pro Tyr Asp Pro Phe
        130                 135                 140

GAT CGC AGT CAC TTG AAA                                                   450
Asp Arg Ser His Leu Lys
145                 150

(2) INFORMATION FOR SEQ ID NO:14:

(i) SEQUENCE CHARACTERISTICS:
        (A) LENGTH: 150 amino acids
        (B) TYPE: amino acid
        (D) TOPOLOGY: linear (ii) MOLECULE TYPE: protein (xi) SEQUENCE DESCRIPTION: SEQ ID NO:14:

Arg Pro Tyr Lys Glu Lys Pro Ile Gln Asn Gln Ala Lys Ser Val Asp
 1               5                  10                  15

Val Glu Tyr Thr Val Gln Phe Thr Pro Leu Asn Pro Asp Asp Asp Phe
            20                  25                  30

Arg Pro Gly Leu Lys Asp Thr Lys Leu Leu Lys Thr Leu Ala Ile Gly
        35                  40                  45

Asp Thr Ile Thr Ser Gln Glu Leu Leu Ala Gln Ala Gln Ser Ile Leu
    50                  55                  60

Asn Lys Asn His Pro Gly Tyr Thr Ile Tyr Glu Arg Asp Ser Ser Ile
65                  70                  75                  80

Val Thr His Asp Asn Asp Ile Phe Arg Thr Ile Leu Pro Met Asp Gln
                85                  90                  95

Glu Phe Thr Tyr Arg Val Lys Asn Arg Glu Gln Ala Tyr Arg Ile Asn
            100                 105                 110

Lys Lys Ser Gly Leu Asn Glu Glu Ile Asn Asn Thr Asp Leu Ile Ser
        115                 120                 125

Glu Lys Tyr Tyr Val Leu Lys Lys Gly Glu Lys Pro Tyr Asp Pro Phe
        130                 135                 140

Asp Arg Ser His Leu Lys
145                 150
```

BACTERIAL FIBRIN-DEPENDENT PLASMINOGEN ACTIVATOR

RELATED APPLICATION

This application claims priority from provisional application Ser. No. 60/069,497 filed Dec. 15, 1997, which is hereby incorporated by reference herein.

GOVERNMENT FUNDING

Work described herein was supported in part by funding from the National Institutes of Health. The United States Government has certain rights in the invention.

TECHNICAL FIELD

The present invention relates to modifications of streptokinase and other microbial enzymes for use to activate plasminogen in the presence of fibrin, to efficiently dissolve an unwanted blood clot in a subject.

BACKGROUND ART

Clinical studies of acute coronary thrombosis have established that administration of plasminogen (Pg) activators such as recombinant tissue plasminogen activator (t-PA) and streptokinase (SK) saves lives and reduces morbidity. Comparison of the efficacy of SK (administered according to a 30 year old dosing regimen) and t-PA (administered by a variety of different protocols), in the presence and absence of heparin, showed that SK is markedly cheaper and can cause less cerebral bleeding than t-PA, whereas t-PA appears to be slightly better at reducing mortality than SK, at least as it is currently administered (e.g. GUSTO, New Engl. J. Med. 329:1615–1622, 1993).

However, problems with administration of these thrombolytic agents remain. For example, acute myocardial infarction patients receiving early administration of either t-PA or SK failed to show reperfusion within 90 min, and reperfusion was not observed in 45–67% of patients (Karagounis L., Amer. Coll. Cardiol. 19:1–10 (1992), Lincoff A., et al. Am J Cardio; 75(14):871–766 (1995); Simes R., et al. Circulation 91(7):1905–1907 (1995)). Failed reperfusion is associated with an approximately double mortality rate from myocardial infarction compared to successful reperfusion, and significantly increases morbidity in surviving patients. The results of thrombolytic therapy as a treatment for venous thromboembolism are also relatively disappointing. Further, the mortality rate for pulmonary embolism appears not to have changed in ~30 years, and no Pg activator has been shown to change the death rate in these patients (Goldhaber S., Chest 107:45S–51S (1995)). When administered to patients with pulmonary embolism, t-PA restores blood flow to only ~33% of occluded lung segments within 24 hours (Goldhaber S., Lancet 2:886–889 (1986)). Similar results have been described with other agents (UPET, Circulation 47:1–108, 1973). In cases of deep venous thrombosis, about two-thirds of patients treated with SK or t-PA have minimal or no lysis of the clot on repeat venography after 24 hours (Salzman E., et al. Basic Principles and Clinical Practice; 3rd Ed. Uppincott, Philadelphia (1994); Goldhaber S. Am J Med 88:235–240 (1990)), thus neither SK nor t-PA treatments are optimal for thrombotic disease in patients.

One property that diminishes the effectiveness of SK as a therapeutic agent is that the administered SK can complex as an antigen with preexisting anti-SK antibodies that are found generally in the human population as a result of prior streptococcal infection. The presence of anti-SK antibodies reduces the efficacy of SK as a thrombolytic agent by quenching Pg activation and increasing the clearance of the protein (Fletcher, A. J Clin Invest 37:1306–1315 (1959)). Thus, the presence of neutralizing human anti-SK antibodies inhibits the formation of a plasminogen activator complex. Antigenicity of SK can be remediated by identification as and elimination or reduction of epitopes by, e.g., genetic deletion (WO 94/07992) of as many structural features of $SK_c$ that do not contribute to Pg binding and activation in the presence of fibrin.

Another property of SK that limits its potency and efficacy as a thrombolytic agent is its rapid proteolytic cleavage during Pg activation, which inactivates the SK-plasminogen activator complex (SK-PAC). An alteration by mutation of SK, e.g. one or more point mutations that removes a proteolytic cleavage substrate site (see WO 96/41883, the contents of which are hereby expressly incorporated by reference) can be made to eliminate cleavage and inactivation during Pg activation, and these alterations can be combined also with an alteration that is a deletion of an antigenic site on SK (WO 94/07992) in a region of the protein that is not involved in SK binding to Pg.

Finally, widespread Pg activation by SK throughout the circulation, rather than SK activation limited to association with a clot, squanders the effectiveness of SK administered as a thrombolytic agent A novel modified SK with enhanced activity, particularly with activity limited to activation of Pg in the presence of fibrin, is desirable.

The practice of the present invention will employ, unless otherwise indicated, conventional techniques of cell biology, cell culture, molecular biology, microbiology, recombinant DNA, and immunology, which are within the skill of the art. Such techniques are explained fully in the literature. See, for example, Molecular Cloning A Laboratory Manual, 2nd Ed., ed. by Sambrook, J. et al. (Cold Spring Harbor Laboratory Press (1989)); DNA Cloning, Volumes I and II (D. N. Glover ed., 1985); Oligonucleotide Synthesis (M. J. Gait ed. (1984)); Mullis et al U.S. Pat. No. 4,683,195; Nucleic Acid Hybridization (B. D. Hames & S. J. Higgins eds. (1984)); *Bacillus subtilis* and Other Gram-Positive Bacteria: Biochemistry, Physiology and Molecular Genetics (Sonenshein, A et al., American Society for Microbiology, Washington, D.C. (1993)); Genetic Manipulation of Streptomyces: a Laboratory Manual (Hopwood, D. et al., Eds., John Innes Foundation, Norwich, England (1985)); the treatise, Methods In Enzymology (Academic Press, Inc., N.Y.); Immunochemical Methods In Cell And Molecular Biology (Mayer and Walker, eds., Academic Press, London (1987)); and Handbook Of Experimental Immunology, Volumes I–IV (D. M. Weir and C. C. Blackwell, eds. (1986)).

Unless otherwise defined, all technical and scientific terms used herein have the same meaning as commonly understood by one of ordinary skill in the art to which this invention belongs. Although methods and material similar or equivalent to those herein can be used in the practice of testing of the present invention, the preferred methods and material are described below. All publications, patent applications, patents and other references mentioned herein are incorporated by reference. In addition, the materials, methods and examples are illustrative only and not intended to be limiting.

SUMMARY OF THE INVENTION

The invention disclosed herein relates to alterations of a bacterial protein, for example, a streptokinase, that render plasminogen activation by the altered protein substantially dependent on the presence of fibrin, for optimization of use as a thrombolytic agent at lower effective dosages than were heretofore possible, which enables more rapid administration with fewer concomitant side effects.

Accordingly, in one embodiment, the invention provides a pharmaceutical composition for dissolving blood clots in a subject, comprising an isolated fibrin-dependent bacterial protease, for example, a modified streptokinase, for example, a modified streptokinase that is substantially pure. A preferred embodiment of the invention is an effective dose of a streptokinase that is substantially pure, and in another embodiment, streptokinase that is substantially pure and in a pharmaceutically acceptable carrier. In another embodiment, the invention provides a pharmaceutical composition wherein the bacterial protease is a modified staphylokinase.

In a preferred embodiment of a modified streptokinase, the streptokinase activation of plasminogen is at least ten-fold greater in the presence of fibrin than in the absence of fibrin, and in another embodiment, the streptokinase activation of plasminogen is at least hundred-fold greater in the presence than in the absence of fibrin. In one embodiment, the modification of the streptokinase is an alteration in the amino terminus selected from the group consisting of mutation, chemical treatment, or enzymatic treatment. The mutation can be selected from the group consisting of deletion, insertion, transposition, and substitution. The enzymatic treatment can be a proteolytic treatment. In a preferred embodiment of a modification of the streptokinase, the mutation is a deletion, for example, a deletion in the amino terminus, for example, a deletion of at least one of the amino acid residues 1–148. Another preferred embodiment of the invention is a pharmaceutical composition having the protein encoded by the mutation produced as a fusion protein, for example, a fusion of the protein having at its amino terminus the maltose binding protein. In a further preferred embodiment, the fusion protein can be engineered to have a factor Xa proteolytic cleavage site located so that the bacterial protein that induces fibrin-dependent plasminogen activation can be removed from the maltose binding protein.

In a preferred embodiment of the invention, the deletion produces an amino terminus selected from the group consisting of residues 24, 60, 65, 144, and 149. In another embodiment of the pharmaceutical composition, the modified streptokinase has a carboxy terminus selected from the group consisting of residues 293, 386 and 414.

In a preferred embodiment, the invention is a composition comprising an isolated modified streptokinase, the modification being removal of amino acid residues in the amino terminus. In this embodiment, the modified streptokinase is a fibrin-dependent kinase, for example, an isolated streptokinase that is substantially pure, and in a further embodiment, an effective dose of an isolated streptokinase that is substantially pure.

The invention in yet another embodiment is method for dissolving a blood clot in a subject, comprising administering to the subject a bacterial fibrin-dependent plasminogen activator. For this method, the subject can be a patient with a thrombotic condition selected from the group consisting of myocardial infarction, venous thrombosis, pulmonary embolism, cerebral thrombosis, graft thrombosis, and arterial thrombosis. In this embodiment, plasminogen activation can be at least ten-fold greater in the presence than in the absence of fibrin. In a preferred embodiment, a method of the invention can be administering a modified streptokinase.

The modified streptokinase can have an alteration produced by genetic mutation, chemical treatment, or enzymatic treatment of the streptokinase. The enzymatic treatment is for example a proteolytic treatment.

In another embodiment, the method can be administering a composition including a substantially pure bacterial fibrin-dependent plasminogen activator, for example, administering a bacterial fibrin-dependent plasminogen activator in an effective dose.

In yet another embodiment, the invention provides a method for dissolving a blood clot in a subject, comprising administering to the subject a streptokinase polypeptide having an alteration of at least one residue from the amino terminus, for example, an alteration which has a mutation of at least one of the amino acid residues of amino acids 1–148 shown in SEQ ID NO: 6, for example, an alteration which has a mutation of at least one of the amino acid residues of amino acids 1–59 shown in SEQ ID NO: 6. The alteration can produces a streptokinase polypeptide having an amino terminus selected from the group consisting of residues 24, 59, 60, 65, 144, and 149 of SEQ ID NO: 6, and a carboxy terminus selected from the group consisting of residues 293, 386 and 414 of SEQ ID NO: 6. In a preferred embodiment, the alteration produces a streptokinase polypeptide having an amino terminus which is residue 144 and a carboxy terminus which is residue 293 as shown in SEQ ID NO: 14. In another preferred embodiment, the streptokinase polypeptide has an amino terminus which is residue 59 and a carboxy terminus which is residue 414 as shown in SEQ ID NO: 12.

Another embodiment of the method includes administering a streptokinase polypeptide with an amino acid sequence which is at least 50% homologous to an amino acid sequence of SEQ ID NO: 6, for example, at least 75% homologous to an amino acid sequence of SEQ ID NO: 6, at least 95% homologous to an amino acid sequence of SEQ ID NO: 6 or at least 99% homologous to an amino acid sequence of SEQ ID NO: 6. In another aspect of this embodiment, the method includes use of the streptokinase polypeptide which has at least one amino acid substitution that inactivates a substrate site for proteolytic cleavage, so that the inactivation of at least one proteolytic cleavage site reduces rate of degradation of the streptokinase polypeptide at least two fold. Further, the streptokinase polypeptide can have at least one naturally occurring polymorphic allele variant amino acid residue.

Another embodiment of the invention is a method for dissolving a blood clot in a subject, comprising administering to the subject a fibrin-dependent streptokinase polypeptide having an amino acid residue sequence encoded by an isolated nucleic acid which hybridizes specifically under stringent conditions to a probe having a nucleotide sequence shown in SEQ ID NO: 5. An expression vector comprising this nucleic acid, and a host cell transformed with this expression vector are also embodiments of the invention. In a preferred embodiment, the host cell is selected from the group consisting of a cell of an Escherichia, a Bacillus, a Streptomyces, a Streptococcus, a Saccharomyces, a Pichia, an insect, a bird, a mammal, and a plant.

In yet another embodiment, the invention provides a nucleic acid encoding a bacterial protease which is a modified streptokinase polypeptide, and a nucleic acid encoding a streptokinase having a deletion producing an amino terminus selected from the group consisting of residues 24, 60, 65, 144 and 149, and a carboxy terminus selected from the group consisting of residues 293, 386 and 414.

DETAILED DESCRIPTION OF PREFERRED EMBODIMENTS

Figure 1:
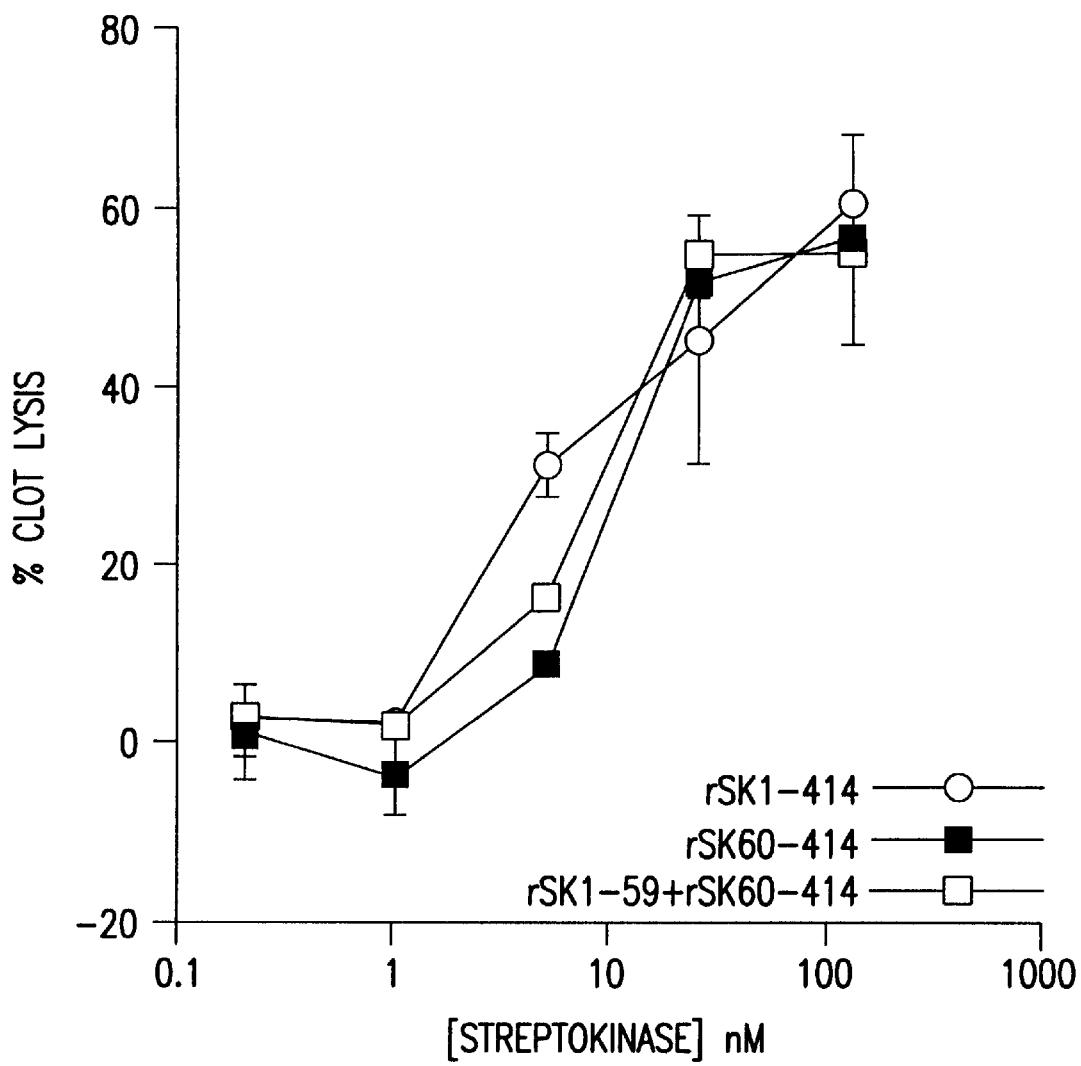
FIG. 1 is a graph which shows the effects of a deletion of residues 1–59 from the amino terminus of streptokinase (SK) on fibrinolysis of human plasma clots. Native streptokinase (rSK1-414, open circles), deletion mutant lacking terminal residues 1–59 (rSK60-414, closed squares), or a stoichiometric mixture of rSK60- 414 and rSK1-59 (open squares), was added to the substrate ($^{125}$I-fibrinogen), and fibrinolysis was measured as the release of soluble fibrin degradation products after 4 hrs of incubation at 37° C.

Unless the context otherwise requires, the terms and phrases defined below as well as throughout this description, shall be understood to have the meanings set forth, for purposes of both this description and the following claims.

The term "streptokinase" (SK) shall mean a protein isolated from a streptococcal species that activates plasminogen (Pg) to produce plasmin which causes liquifaction of fibrin and dissolution or lysis of a thrombus (blood clot). The term "SK$_c$" designates the particular SK isolated from bacterial cells of the Lancefield Group C strain *S. equisimilis* H46A. Native SK (nSK) is identical in amino acid residue sequence to that elaborated by a species or strain of the Gram-positive bacterium genus Streptococcus. "Recombinant" SK (rSK) as used herein refers to SK that is isolated as expressed from a recombinant cell, e.g., a microbial cell, e.g., an *Escherichia coli* cell, or in a eukaryotic cell such as a yeast or an insect cell, which cell is transformed with a vector bearing a gene that encodes, for example, an SK or SK variant protein.

The term "thrombus" shall mean a clot formed in the circulation of the cardiovascular system from blood constituents, and contains fibrin, and includes without reservation a blood clot that can be located in any tissue or organ such as heart, brain, vein, artery, and lung.

The term "fibrin" shall mean the product of fibrinogen produced by action of thrombin during the clotting or coagulation of blood, and found in blood clots.

The phrase "dissolution" or "lysis" or "dissolving" of a blood clot a reduction in size or elimination of a bloodclot from a subject.

The term "subject" shall mean a living animal or human in need of therapy for, or susceptible to, a condition of thrombosis or its sequelae such as myocardial infarction, which condition is remediable or alleviated through dissolution or lysis of a thrombus. In preferred embodiments, the subject is a mammal, including humans and non-human mammals such as dogs, cats, pigs, cows, sheep, goats, horses, rats, and mice. In the most preferred embodiment, the subject is a human. The term "subject" does not exclude an individual that is normal in all respects. The subject may be a candidate for future treatment by clot lysis, having formerly been treated surgically or by therapy with an agent that dissolves clots, and may be under treatment with such an agent.

The term "patient" shall mean a human subject who has presented at a clinical setting with a particular symptom or symptoms suggesting the need for treatment with a thrombolytic agent. Patient's symptoms can be indicative of thrombotic conditions (in at least one anatomical site), such as myocardial infarction (heart), venous thrombosis (vein), pulmonary embolism (lung), cerebral thrombosis (brain), graft thrombosis (implanted graft), and arterial thrombosis (artery), e.g. coronary thrombosis (coronary artery). A patient's diagnosis can alter during the course of disease progression, such as development of further disease symptoms, or remission of the disease, either spontaneously or during the course of a therapeutic regimen or treatment.

The term "fibrin-dependent" refers to the proteolytic activity of a bacterial enzyme, for example, that of a variant of a bacterial protein which induces fibrin-dependent plasminogen activation, for example, a variant streptokinase, for example, an amino terminal deletion mutant protein, which substantially activates Pg in the presence of fibrin compared to in the absence of fibrin. Activation of Pg in the absence of fibrin is slight, such that activation of Pg is at least 5-fold greater than in the presence of fibrin compared to in the absence, more preferably 10-fold greater, more preferably 25-fold greater, and even more preferably 50-fold greater, as measured by enzyme kinetic methods known to one of skill in the art, and described in the Examples herein.

The term "alteration" or "modification" refers to a change in the chemical composition of a bacterial protein which induces fibrin-dependent plasminogen activation, for example, an SK or SK fragment, and includes without limitation changes by mutation of the gene encoding a bacterial protein which induces fibrin-dependent plasminogen activation, for example, the SK, and enzymatic and chemical treatment of SK protein. An altered bacterial protein which induces fibrin-dependent plasminogen activation, for example, an SK or SK fragment, can be produced synthetically by organo-chemical peptide synthesis. The "altered derivative" obtained by genetic mutation includes SK polypeptides that result from one or more of the processes of deletion, substitution, transpostion, translocation, insertion, and point mutation of a gene encoding a bacterial protein which induces fibrin-dependent plasminogen activation, for example, encoding SK. The altered derivative may be obtained also by chemical or enzymatic modification of a bacterial protein which induces fibrin-dependent plasminogen activation, for example, an SK protein, for example by proteolytic digestion with trypsin. The altered derivative includes without limitation, one or more changes resulting from the presence of naturally occurring polymorphisms, alleles, fragments, analogues, chemical derivatives and conjugates, enzymatically obtained derivatives and conjugates, and derivatives that vary in such post-translational modifications as glycosylation and phosphorylation.

The phrase "derivative with modified function" or "altered derivative" a bacterial protein which induces fibrin-dependent plasminogen activation, for example, an SK molecule, that possesses a useful biological activity that is substantially different from that of the native protein not having a fibrin-dependent plasminogen activator activity, for example, nSK. The biological activity of the altered derivative of the bacterial protein, for example, of the altered nSK, is substantially similar to a biological activity of another thrombolytic agent, for example, that of recombinant t-PA. In a preferred embodiment, the "modified function" refers to the property of fibrin dependence. Modified function can also refer to other properties such as resistance to proteolytic degradation or improved thermal stability.

The term "variant" shall mean a protein or nucleic acid molecule that is substantially similar in structure and biological activity and may substitute for the molecule of which it is a variant. Thus, provided that two molecules possess a common activity and may substitute for each other, they are considered variants even if the composition or secondary, tertiary or quaternary sturcture of one of the molecules is not identical to that found in the other, or if the amino acid or nucleotide sequence is not identical.

The term "fragment" with respect to a molecule such as a bacterial protein which induces fibrin-dependent plasminogen activation or the gene encoding this protein, for example, an SK protein or a nucleic acid encoding SK, refers to a portion of a native or variant bacterial protein such as the SK amino acid residue or nucleotide sequence. The term "fragment" includes a chemically synthesized protein fragment, for example, of SK.

The term "effective dose" means that amount of a composition such as a fibrin-dependent bacterial protein or SK that is provided to achieve a therapeutic effect in clot dissolution or reduction in size of a clot An equipotent dose of an altered bacterial protein which induces fibrin-dependent plasminogen activation, for example, an altered SK, achieves the same medical endpoint as a larger dose of the native or unmodified protein. Equipotency of the much smaller dosage of the altered bacterial protein, for example, SK compositions of the invention can be due to one or more mechanisms resulting from specific alterations, alone or in combination. These mechanisms include: Pg activation restricted to SK in the presence of fibrin; decreased antigenicity of SK; increased stability of SK; and decreased plasmin proteolysis of SK. The equipotency of altered SK as invented here is not limited to any one particular mechanism or combination of mechanisms.

The terms "protein," "polypeptide" and "peptide" are used interchangeably herein.

The term "culture medium" refers generally to any preparation suitable for cultivating living cells. A "cell culture" refers to a cell population sustained in vitro.

More Americans die from a thrombotic occlusion of a coronary or cerebral artery than any other single cause of mortality. The plasminogen activator SK derived from various streptoccal species is widely used to dissolve blood clots. Unlike the naturally occurring human plasminogen activators urokinase and tissue plasminogen activator (t-PA), SK has no intrinsic enzymatic activity (reviewed in Reddy, K., Enzyme 40:79–89 (1988)). Interest in SK and plasminogen (Pg) activators was stimulated by studies showing that coronary artery thrombosis was present in patients suffering an acute heart attack (DeWood M. A., et al. N Engl J Med 303:897 (1980)). Further, in these patients, instilling streptokinase produced from Group C streptococci into the coronary artery, could dissolve the thrombus (Markis J. E., et al. N Engl J Med 305:777 (1981)) and restore blood flow to the heart. The landmark GISSI study (Lancet 1:397–402 (1986)) proved that SK saved lives in patients suffering an acute myocardial infarction.

Fibrinolysis (clot dissolution, clot lysis) is the process of degrading a blood clot (thrombus) through proteolytic cleavage of its fibrin meshwork. The key activity of a proteolytic enzyme on a protease precursor (zymogen) in this process is that of Pg conversion to plasmin (Pn), whose function is specifically modulated by protein-protein interactions with inhibitors, e.g., α2-antiplasmin, and activators, e.g., the endogenous tissue Pg activator (t-PA), the bacterial agent SK and others. In normal physiology, the biologically and medically important interaction is that between Pg-Pn and the indirect Pg activator SK. SK converts Pg (without cleavage) into a catalytically efficient Pg activator. At least three functional steps are known in this process: SK forming a tight stable activator complex with Pg or Pn; SK generating or unmasking the latent active site in Pg creating a 'virgin enzyme' (Pg*); and SK modifying the substrate specificity of Pg* or Pn so that the complex can cleave Pg molecules.

The in vivo complex of the streptokinase isolated from Lancefield group C streptococcal species *S. equisimilis* H46A (SK) with Pg (the plasminogen activator complex $SK_c$-PAC) is a catalytically efficient Pg activator. However because Pg activation by $SK_c$ does not require cofactors such as fibrin, $SK_c$ can cause rapid activation of Pg throughout the circulation (Sherry S., Clin Cardiol 13:3–10 (1990)). Thus Pg activation by $SK_c$ in the blood is rapid and unregulated (Marder V. J., et al. N Engl J Med 318:1512–1520 (1988); Marder et al., N Engl J Med 318:1585–1595 (1988)). This squanders the fibrinolytic effect of both the administered $SK_c$ and the active Pn produced from the complex, and leads to general plasminolysis of coagulation proteins such as fibrinogen.

Indirect Plasminogen Activation by Streptokinase

Pg is a catalytically inactive zymogen, and naturally occurring mammalian Pg activators, t-PA and u-PA, are serine proteases which activate Pg by direct enzymatic cleavage of an Arg561-Val peptide bond. This cleavage yields Pn, also a serine protease, which functions to specifically cleave fibrin chains in a thrombus.

In contrast to mammalian activators, the bacterial protein SK indirectly activates Pg by a nonproteolytic mechanism. $SK_c$ is a single chain protein with no identified intrinsic enzymatic activity, and forms an enzymatic "activator complex" with Pn, altering its function towards the cleavage of substrate Pg molecules (Castellino, F. J. Semin Thromb Hemost; 10:18–23 (1984); Collen D., et al. Blood; 84:680–686 (1994); Reddy, K. N. Enzyme; 40:79–89 (1988)).

SK binds tightly to human Pg, which is itself inert as an enzyme, to form an SK-Pg complex. Although the present invention is not limited to a particular mechanism of action of SK, the following steps are generally used to describe activation of Pg. Shortly after formation of the SK-Pg complex, a titratable active site appears in the Pg moiety of the SK-Pg complex, without cleavage of the Pg Arg(561)-Val bond, creating a "virgin" Pg enzyme (Pg*). SK-PAC binds and cleaves Pg but is inefficient at cleaving other substrates like casein or fibrin (Reddy K. N. N., et al. J.Biol.Chem. 247:1683–1691; Schick, LA et al. Biochemistry 12:4315–4321 (1973); Kline D. L., et al. J. Biol. Chem. 236:2807–2812 (1961)). In contrast, Pn can not activate Pg, but efficiently cleaves casein and fibrin.

Although SK-PAC is a catalytically efficient Pg activator, it does not require cofactors such as fibrin, so it rapidly activates Pg throughout the circulation (Sherry S. Clin Cardiol 13:3–10 (1990)).

Structure of Streptokinase

Studies of the whole molecule by NMR spectroscopy (Teuten A., et al., Biochem J. 290:313–319 (1993)) and of different proteolytic fragments of SK (Parrado, J., et al. Prot. Sci. 5: 693–704 (1996)) showed that SK exists as a folded globular structure at physiological temperature and pH. This structure appears to unfold in a pattern suggestive of the existence of at least three (Teuten A. J., et al., supra; Parrado J., et al. supra) or four domains (Damaschun G., et al. Eur.

Biophys. J. 20:355–61 (1992)) that have different independent stability and interdomain flexibility. The amino terminal region of the molecule, spanning residues 1–63, appears to be relatively unstructured as does the Carboxy terminus of the molecule, spanning residues 381–414 (Teuten A. J., et al, supra; Parrado J., et al., supra). The three identifiable domains of SK appeared to be relatively intact in fragments spanning 1–146, 147–287 and 288–380. The amino terminal domain consists of two fragments, 1–63 and 64–146 which, when bound together appeared to form a compact domain (Parrado J., et al. supra), but when separated, appear unstructured. None of the three domains alone was active in Pg activation, though the central and carboxy terminal domains together had trace activity which was estimated to be decreased by 6000-fold compared to intact SK. Previous studies indicate that SK1-59 and SK60-386 associate with each other after cleavage, an association that does not require Glu-Pg because it can be detected also when SK is cleaved by trypsin in the absence of Pg (Misselwitz, R. et al. J. Biol. Macromolec. 14:107–116 (1992)). Even when the SK1-59 and SK60-386 fragments have been dissociated, they appear to reassociate in a functionally significant fashion (Shi, G. et al. Thromb Res.58:317–29 (1994); Parrado et al., supra).

Thus the embodiment of the invention of an SK polypeptide that has an alteration such as a mutation, e.g., a deletion affecting amino terminal residues, e.g., residues 1–59, which is an efficient Pg activator in the presence of fibrin but not in the absence of fibrin, is surprising in view of previous studies showing markedly reduced (~6,000-fold) function of the fragment lacking the amino terminal as an indirect Pg activator.

Polymorphisms of SK

Recent studies have identified DNA sequence polymorphisms, which are naturally occurring sequence variations in genes from different members of natural populations, in SK cDNAs obtained from 27 different human Streptococcus sp. isolates (Kapur V. et al. Molec. Microbiol. 16: 509–519 (1995)). There is high DNA sequence variability in two regions of genes for SK (Huang, T.-T., et al., Mol. Microbio. 3: 197–200 (1989); Johnston, K. et al. Zentral. Bakt. Suppl. 22: 339–342 (1992); Malke, H. et al. Gene. 34:357(1993); Kapur et al., supra). When the gene sequences are translated, the protein sequences of the polymorphisms similarly show a pattern of strong variability in the regions spanning residues 46–70 and 78–85. However, the remaining 381 amino acid residues (92% of the molecule) are strongly conserved within the natural population. Since all the SKs tested are active indirect Pg activators, it seems likely that the residues in variable regions are found in features of the protein that do not function to interact with Pg. These residues may function as linkers, spacers or conformation stabilizers that permit the conserved regions of $SK_c$ to functionally interact with Pg. A novel SK produced by a strain of S. equisimilis of nonhuman origin shows significant sequence heterogeneity in the amino terminus of SK compared to the sequences of previously described SK genes Nowicki, S. et al., Thromb. Haemost. 72:595–603 (1994)), presenting yet additional naturally occurring polymorphic alleles of SK.

Malke et al. (Zbl. Bakt. 278:246–257 (1993)) lists naturally occurring streptococcal allelic amino acid substitutions found at many residues in mature SK from isolates belonging to Lancefield Groups A and G, and the frequency at which each of the alleles was found among the natural population of streptococci sequenced SK genes. Alleles of the amino acid sequence used as a reference standard (SK gene of S. equisimilis H46A, see e.g. the nucleotide sequence of the gene in SEQ ID NO: 5, and SEQ ID NO: 6 for the amino acid residue sequence) suitable for substitution mutations which are preferred embodiments of the invention include, but are not limited to the following: thr24ile (using a designation of the amino acid and residue number for SK as sequenced from S. equisimilis H46A, followed by the substitution amino acid), asn30asp, gln31lys, asp32lys, asp32gly, ile33val, ser34phe, leu35ile, lys36asn, arg45gln, pro62leu, ser71pro, dlu85lys, asp96gly, lys121arg, gly123asp, thr129ile, leu137val, ser138lys, arg144lys, lys147gln, glu148pro, pro150ala, ile151val, gln152his, gln154ser, lys156glu, ser157arg, asp159asn, glu161asn, thr163glu, gln165ser, thr167val, pro168ser, leu169glu, asn170thr, pro171gly, asp172asn, asp173leu, arg176thr, gly178leu, gly178ser, gly178ala, lys180arg, asp181asn, asp181glu, thr182gln, thr182arg, lys183tyr, leu184his, lys186thr, ile190val, thr193ser, ile194leu, thr195ser, leu200ala, gln202ile, ser205phe, asn208ser, asn210thr, asn210lys, asn210gln, gly213asp, thr215ile, tyr217thr, glu218lys, arg244his, val245ile, asn247asp, arg253glu, arg253lys, ile254ala, lys256pro, lys256ser, ser258thr, leu260ile, asn261ile, asn261thr, ile270val, lys279gln, lys281glu, lys298asn, asp303asn, glu306lys, arg319gly, gly344asp, asp347asn, asp359asn, asp360lys, thr361asn, ile364val, ile365val, gly374lys, glu376ala, asn377lys, ala378gly, glu395lys, val396ala, and asn411lys.

This list is for illustrative purposes only, and is not intended to exclude other polymorphic alleles of SK, for example, arg401pro described by Young et al. (J. Biol. Chem 270: 29601–29606 (1995)).

Proteolytic Cleavage of SK during Pg Activation

Shortly after forming the $SK_c$-PAC, the $SK_c$ moiety is rapidly cleaved at several sites (Brockway, W. et al. Biochemistry 13:2063–2070 (1974); McClintock D. et al. Biochem. Biophys. Res. Commun. 43:694–702 (1974); Markus G., et al., J Biol Chem 251:6495–6504 (1976); Siefring, G. et al., J Biol Chem 251:3913–20 (1976)). This cleavage is associated with a significant decline (at least 80%) in the apparent catalytic efficiency of the SK-PAC (Markus et al., supra). Most of the rapidly formed SK fragments are unstable, and generate a series of more stable fragments. The stable fragments formed during Pg activation have been isolated and studied (Brockway et al., supra; McClintock D. et al. Biochem. Biophys. Res. Commun.43:694–702 (1974); Siefring et al., supra) as have SK fragments produced by trypsin and thermolysin (Misselwitz et al., supra, 1992), chymotrypsin (Parrado et al., supra) and immobilized Pn (Shi, et al 1994).

SK is cleaved at the amino and carboxy terminus, at K59 and probably at K386, and at R401. The SK1–59 peptide remains associated with the complex but the carboxy terminal peptides probably do not. SK appears also to be cleaved at K293 and/or at K332 and eventually at K147.

Further, that SK is rapidly cleaved during Pg activation to lower molecular weight forms with substantially less activity, i.e., reduction of the function of the activator complex by as much as 1500-fold within a few minutes, is also a likely cause of suboptimal thrombolysis seen in patients treated with SK. Further negative sequelae include rapid activation by SK-PAC of Pg in the blood in the absence of fibrin (Sherry S., Clin Cardiol 13:3–10 (1990)) at sites distant from the thrombus, which generates Pn that can cleave circulating clotting factors like fibrinogen, factor V and factor VIII, instead of fibrin in a clot (Marder V. J., et al., N Engl J Med 318:1512–1520 and 1585–1595 (1988)).

Moreover, circulating Pn is more susceptible to inhibition by α2-antiplasmin and a2-macroglobulin, which can quench its thrombolytic effects (Lijnen et al. Baillieres Clinical Haematology 8:277–90 (1995)).

Modification of a fibrin-dependent SK that has been altered in the Amino terminus, to achieve also a reduced level of proteolytic cleavage of SK during the Pg activation process can be performed by one of ordinary skill in the art, e.g., by the methods of WO 96/41883. The proteolytic degradation of SK obtained by such alteration can be two-fold slower, preferably four-fold slower, even more preferably eight-fold slower rate of degradation, as determined by comparison to loss of the full-length SK species (47 kDa for that of $SK_c$) and appearance of smaller proteolytic fragments on an SDS-PAGE gel.

Modifications that reduce the rate of proteolytic cleavage of SK include but are not limited to one or more of the following alterations (indicated by the formula showing respectively the amino acid found in $nSK_c$, the residue number, and the substituted amino acid): lys36ala, arg45ala, lys51ala, lys59ala, lys61ala, lys147ala, arg232ala, lys257ala, lys298ala, lys309ala, lys333ala, arg363ala, lys371ala, lys386ala, lys394ala, arg401ala. Additionally, a different uncharged small aliphatic amino acid may be substituted into SK instead of the aforementioned substitutions other than ala can be used, for example, gly or ser, in one or more of the residues, to confer improved stability of the altered SK to proteolysis upon Pg activation, e.g., lys36gly, etc.

Further, the substituted sites can be used in multiple combinations, e.g., multiple substitutions comprising an SK having more than one of lys36ala, arg45ala, lys51ala, lys59ala, and lys386ala, and in each case ala, ser or gly can be used. Thus elimination of one or more site of proteolytic destruction of SK can be introduced in singly or in combination, and in combination with an amino terminus alteration conferring fibrin-dependence for Pg activation.

Antigenic Determinants of the SK Protein

Preexisting anti-SK antibodies found in blood of humans because of widespread prior streptococcal infections reduce the efficacy of SK as a thrombolytic agent by binding and clearance of SK from circulation (Fletcher, A J Clin Invest 37:1306–1315 (1959). Monoclonal antibodies and recombinant SK fragments (Reed, G. et al, J. Immunl. 150: 4407–4415 (1993)) have been developed for mapping epitopes, and several epitopes can be associated with specific sequences of amino acid residues, e.g., amino acid residues 1–13 (Parhami-Sereni, B., et al., Hybridoma 15: 169–176 (1996)), and more specifically, amino acid residues 3–7 and 59–63 (Parhami-Sereni, B., et al., J. Mol. Biol. 271:333–341 (1997)).

Antigenicity of SK can be remediated by alteration of such epitopes following identification, e.g., genetic deletion (see WO 94/07992, the contents of which is hereby expressly incorporated by reference). The amino terminus alterations producing the feature of fibrin-dependence in an SK polypeptide can have the additional beneficial effect of reducing antigenicity by elimination of one or more antigenic determinants or epitopes.

The unregulated or untargeted indirect Pg activation at sites distant from the thrombus that squanders the fibrinolytic effects of Pn and reduces effectiveness of SK as a therapeutic agent are mitigated by the amino terminal alterations that are preferred embodiments of the present invention. Modification of SK to eliminate or reduce Pg activation in the absence of fibrin, to eliminate or reduce antigenic determinants, and to reduce proteolytic cleavage of SK during the activation process is a rational design for a more potent therapeutic agent having the advantages of longer time of in vivo efficacy, fewer side effects such as antigenicity, application to a larger number of thrombotic conditions, and reduced dosage requirements.

Genes, Nucleic Acids, Hybridization to Clone Homologs of SK, and Expression Vectors Homologs of the fibrin-dependent SK proteins can be generated by mutagenesis, for example, a point mutation causing a substitution or a deletion. For instance, mutation can give rise to homologs which retain substantially the same biological activity of the SK from which it was derived. A protein is considered to have SK biological activity if it can bind and activate Pg. A protein has fibrin-dependent SK biological activity if it can bind Pg, and activate it to a much greater extent than in the absence of fibrin. Exemplary fibrin-dependent SK proteins are shown in SEQ ID NO: 12 and SEQ ID NO: 14. The SK gene fragments were constructed as described in Reed, G. et al., supra (1993) and Parhami-Sereni, B. et al., supra (1995), using PCR and specific internal primers.

Exemplary nucleotide sequences of genes encoding SK proteins include SEQ ID NO: 1 encoding nSK as a maltose binding protein (MBP) fusion shown in SEQ ID NO: 2; SEQ ID NO: 3 encoding rSK60-414 as MBP fusion shown in SEQ ID NO: 2; and SEQ ID NO: 5 encoding nSK shown in SEQ ID NO: 6. The fusion protein genes have been engineered to be cleaved by use of the protease Factor Xa (New England Biolabs, Beverly, Mass.). In the MBP::nSK fusion protein shown in SEQ ID NO: 2, nSK is cleaved from the MBP moiety of the fusion protein after residue Arg381, yielding an Ile amino terminus. Similarly, in the MBP::rSK60414 fusion protein shown in SEQ ID NO: 4, the rSK60-414 is cleaved from the MBP moiety after the Arg381 residue, producing an amino terminus having Ser. Exemplary nucleotide sequences encoding additional fibrin-dependent SK variants are shown in SEQ ID NO: 11 and SEQ ID NO: 13, encoding rSKS9-414 in SEQ ID NO: 12, and rSK144-293 in SEQ ID NO: 14, respectively.

The term "fusion protein" as used here and in the claims means a non-naturally occurring protein obtained from genetic manipulation of two or more genes encoding respectively amino acid sequences derived from two or more different proteins in the same translational reading frame. Translation of the fusion gene produces a fusion protein, which has protein features of each of the two or more different proteins that contributed to it. Fusion proteins which are preferred embodiments of the present invention comprise at least a component which binds to a fibrin-dependent streptokinase and another protein, for example, a protein useful for bioluminescent or chemoluminescent or radiolabeling detection, or a protein useful because of specific affinity for a ligand.

The term "vector" as used here and in the claims refers to a nucleic acid molecule capable of transporting another nucleic acid to which it has been linked. The term "expression vector" includes any vector, (e.g., a plasmid, cosmid or phage chromosome) containing a gene construct in a form suitable for expression by a cell (e.g., linked to a promoter).

Vectors capable of directing the expression of genes to which they are operatively linked are referred to herein as "expression vectors". Expression vectors for expression of the gene for a fibrin-dependent SK and capable of replication in a cell of a bacterium, such as an Escherichia, a Bacillus, a Streptomyces, a Streptococcus, or in a cell of a simple eukaryotic organism such as the yeast Saccharomyces or Pichia, or in a cell of a eukaryotic multicellular organism such as an insect, a bird, a mammal, or a plant, are within the preferred embodiments of the present invention. Such vectors may carry functional replication-specifying sequences (replicons) both for a host for expression, for example a Streptomyces, and for a host, for example, E. coli, for genetic manipulations and vector construction. See e.g. U.S. Pat. No. 4,745,056. Suitable vectors for a variety of organisms are described in Ausubel, F. et al., Short Protocols in Molecular Biology, Wiley, New York (1995), and for example, for Pichia, can be obtained from Invitrogen (Carlsbad, Calif.).

"Homology" refers to sequence similarity between two peptides or between two nucleic acid molecules. Homology can be determined by comparing a position in each sequence which may be aligned for purposes of comparison. When a position in the compared sequence is occupied by the same base or amino acid, then the molecules are homologous or identical at that position. A degree of homology between sequences is a function of the number of matching or identical positions shared by the sequences.

A "fusion protein" which can be a "chimeric protein" is a fusion of a first amino acid sequence encoding one of the fibrin-dependent SK proteins with a second amino acid sequence defining a domain foreign to and not substantially homologous with any domain of the fibrin-dependent SK proteins. A fusion gene of nSK as a 5' fusion to the 3' end of the gene for maltose binding protein, such as the fusion gene of SEQ ID NO: I that encodes a protein shown in SEQ ID NO: 2, having the amino terminus of nSK linked to the carboxy terminus of maltose binding protein, is used herein for purposes of production of the nSK protein. Following expression of the protein, the fusion protein is purified by affinity chromatography using a column containing a resin to which amylose is covalently linked, or by ion exchange chromatography. The fusion protein gene was engineered by use of an appropriate vector (see the Examples, below) so that the SK protein can be removed from the remainder of the fusion protein by proteolytic digestion with factor Xa (New England Biolabs, Beverly, Mass.).

Similarly, a fusion gene embodiment of the invention is exemplified by: SEQ ID NO: 3, which joins the gene encoding the deletion mutation rSK60-414 as a fusion to the 3' end of the gene encoding maltose binding protein; the fusion encoding a protein which is the amino terminus of mutant rSK60-414 protein is linked to the carboxy terminus of maltose binding protein (SEQ ID NO: 4). Fusion to the MBP gene is used herein for purposes of production of recombinant nSK and modified SK proteins. Thus, the rSK60-414 portion can be removed by proteolytic digestion with Factor Xa.

In one embodiment, the invention includes a nucleic acid which encodes a peptide having at least the preferred embodiment of SK having fibrin-dependent Pg activation. Preferably, the nucleic acid is a cDNA molecule comprising at least a portion of the nucleotide sequence represented in one of SEQ ID NO: 5, and having an alteration such as a deletion in the 5' end of this sequence encoding the carboxy terminus of the SK.

Preferred nucleic acids encode a fibrin-dependent SK protein comprising an amino acid sequence at least 60% homologous, more preferably 70% homologous and most preferably 80%, 90%, or 95% homologous with an amino acid sequence shown in one of SEQ ID NO: 6. Nucleic acids which encode polypeptides having an activity of a subject SK protein and having at least about 90%, more preferably at least about 95%, and most preferably at least about 98–99% homology with a sequence shown in SEQ ID NO: 6 are within the scope of the invention.

Another aspect of the invention provides a nucleic acid which hybridizes under high stringency conditions to a "probe", which is a nucleic acid which encodes a peptide having a portion of an amino acid sequence shown in SEQ ID No: 6. A suitable probe is at least 12 nucleotides in length, is single-stranded, and is labeled, for example, radiolabeled or fluorescently labeled. Appropriate moderate conditions of stringency of conditions of formation of double-strandedness which promote DNA hybridization, for example, 6.0×sodium chloride/sodium citrate (SSC) at about 45° C., are followed by successive washes of increased stringency, e.g., 2.0×SSC at 50° C., and are known to those skilled in the art or can be found in Current Protocols in Molecular Biology, John Wiley & Sons, N.Y. (1989), 6.3.1–6.3.6. Other suitable stringency conditions include selecting the salt concentration in the wash step from a low stringency of about 2.0×SSC at 50° C., and then using a wash of a high stringency condition, of about 0.2×SSC at 50° C. In addition, the temperature in the wash step can be increased from low stringency conditions at room temperature, about 22° C., to high stringency conditions at about 65° C.

Conditions for hybridizations are largely dependent on the melting temperature for half of the molecules of a substantially pure population of a double-stranded nucleic acid, a parameter known as the Tm. For nucleic acids of sequence 11 to 23 bases, the Tm can be calculated in degrees C. as 2(number of A+T residues)+4(number of C+G residues). Hybridization or annealing of the probe to the nucleic acid being probed should be conducted at a temperature lower than the Tm, e.g., 15° C., 20° C., 25° C. or 30° C. lower than the Tm. The effect of salt concentration (in M of NaCl) can also be calculated, see for example, Brown, A., "Hybridization" pp. 503–506, in The Encyclopedia of Molec. Biol., J. Kendrew, Ed., Blackwell, Oxford (1994).

Fragments of the nucleic acids encoding the fibrin-dependent portion of the presently claimed SK proteins are within the scope of the invention. As used herein, a fragment of the nucleic acid encoding the fibrin-dependent portion of an SK protein refers to a nucleic acid having fewer nucleotides than the nucleotide sequence encoding the entire amino acid sequence of an SK protein but which nevertheless encodes a peptide having the biological activity, e.g., fibrin-dependent Pg activation activity of the SK protein. Nucleic acid fragments within the scope of the present invention include those capable of hybridizing under high stringency conditions with nucleic acids from other species for use in screening protocols to detect SK homologs and naturally occurring polymorphic alleles.

Useful expression control sequences, include, for example, the early and late promoters of SV40, adenovirus or cytomegalovirus immediate early promoter, the lac system, the trp system, the TAC or TRC system, T7 promoter whose expression is directed by 7 RNA polymerase, the major operator and promoter regions of phage lambda, the control regions for fd coat protein, the promoter for 3-phosphoglycerate kinase or other glycolytic enzymes, the promoters of acid phosphatase, e.g., Pho5, the promoters of the yeast α-mating factors, the polyhedron promoter of the baculovirus system and other sequences known to control the expression of genes of prokaryotic or eukaryotic cells or their viruses, and various combinations thereof. A useful translational enhancer sequence is described in U.S. Pat. No. 4,820,639.

It should be understood that the design of the expression vector may depend on such factors as the choice of the host cell to be transformed and/or the type of protein desired to be expressed. In one embodiment, the expression vector includes a recombinant gene encoding a peptide having an activity of a fibrin-dependent SK protein. Such expression vectors can be used to transfect cells and thereby produce proteins or peptides, including fusion proteins or peptides, encoded by nucleic acids as described herein.

Dosages and Pharmaceutical Compositions

Two dosage regimens of SK were used in the GUSTO trials for administration to patients with acute myocardial infarction (New Engl. J. Med. 329: 1615–1622 (1993)) for comparison to t-PA: 1.5 million Units (U) of SK (Kabikinase, Kabi Vitrum, Sweden) given over a 60-min period, with subcutaneous heparin (sodium heparin, Sanofi, Paris) in a dose of 12,500 U twice daily, beginning 4 h after initiation of lytic therapy; and SK (1.5 million U) with intravenous heparin administered in an intravenous bolus dose of 5000 U followed by a continuous infusion of 1000 U per h. Potency of a typical batch of SK is found to be 100,000 U/mg. Thus the GUSTO trial administered 15 mg/person/hr. Assuming a patient of 75 kg, the GUSTO dose of SK was 200 µg/kg/hr to a myocardial infarct patient.

Use of SK for treatment of other conditions has followed other regimens, e.g., treatment of deep venous thrombosis has used 250,000 U/dose over 30 min followed by 100,000 U/h for 72 hours (7,450,000 U total). Pulmonary embolism has been treated by 250,000 U for 30 min followed by 100,000 Units/h for 24 h (2,650,000 U total).

The formulations and methods of the preferred embodiments of the invention supply fibrin-dependent streptokinase in doses equipotent to the GUSTO dosage regimens, however substantially smaller doses in molar terms (and in terms of mass) of the fibrin-dependent altered SK variants described herein are required. The preferred equipotent dose can be one-fifth the dose of the native SK (nSK) used in the GUSTO trial, more preferably one-tenth the dose, even more preferably one-twentieth the dose, and most preferably one-fiftieth the dose used in the GUSTO trial. Thus the altered fibrin-dependent SK variants of the invention can be administered in a dose of 40 µg/kg/hr, 20 µg/kg/hr, 10 µg/kg/hr, or most preferably 4 µg/kg/hr, for treatment of myocardial infarct.

A fibrin-dependent variant of SK can be administered to a myocardial infarct patient with the following regimen: 5 µg/kg, 10 µg/kg, 20 µg/kg, 40 µg/kg, 80 µg/kg, 150 µg/kg, 300 µg/kg, 600 µg/kg, up to 10 mg, over a period of 1.5 hours. Dosage at this level can be maintained as necessary up to a 2 hour, 3 hour, or a 4 hour period.

As the dose of fibrin-dependent variant of SK can be administered in substantially smaller mass per dose to obtain equipotency to nSK, it can also be administered in larger quantity in one bolus, or over a more prolonged period of time, to obtain greater effectiveness. An "effective dose" is that amount of fibrin-dependent SK that can be determined to successfully achieve a medical endpoint of clot dissolution or reduction in size, with concomitant reperfusion of distal circulation. An equipotent dose of an altered SK achieves the same medical endpoint as a larger dose of nSK.

As the variants of the present invention can be additionally altered to carry fewer antigenic epitopes, e.g., epitopes found in Amino terminal residues of nSK, the administered variant can cause less reaction with antibodies in human serum. Thus the altered fibrin-dependent SK variants, additionally altered to reduce the number of SK epitopes, can be administered at larger doses than nSK, e.g., can be administered at 60 µg/kg/hr, 80 µg/kg/hr, 100 µg/kg/hr, 150 µg/kg/hr, 200 µg/kg/hr, or even 2 mg/kg/hr.

The fibrin-dependent SK carrying fewer antigenic determinants can be administered to a myocardial infarct patient with the following regimen: 1 mg/kg/hour over each hour for a 72 hour period.

The description herein is not intended to be delimiting with respect to the nature of the therapeutic agent comprising the fibrin-dependent SK, e.g., to a particular route of the administration and additional routes as listed herein.

In a preferred embodiment of the present invention, the fibrin-dependent SK compositions of the invention can be administered by combination therapy, i.e., combined with other agents. The combination therapy can include a composition which is an embodiment of the present invention with at least one other clot lysis agent, exemplified by but not limited to heparin, t-PA, u-PA, staphylokinase, hirudin, aspirin, or with at least one other therapeutic agent unrelated to clot dissolution, such as an antibiotic, antifungal, or other conventional therapy.

As used herein, "pharmaceutically acceptable carrier" includes any and all solvents, dispersion media, e.g., human albumin or cross-linked gelatin polypeptides, coatings, antibacterial and antifungal agents, isotonic, e.g., sodium chloride or sodium glutamate, and absorption delaying agents, and the like that are physiologically compatible. The use of such media and agents for pharmaceutically active substances is well known in the art. Preferably, the carrier is suitable for oral, intravenous, intramuscular, subcutaneous, parenteral, spinal or epidermal administration (e.g., by injection or infusion). Depending on the route of administration, the active compound can be coated in a material to protect the compound from the action of acids and other natural conditions that can inactivate the compound.

The phrases "parenteral administration" and "administered parenterally" as used herein mean modes of administration other than oral and topical administration, usually by bolus injection or infusion, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

Dosage regimens are adjusted to provide the optimum desired response, e.g., a therapeutic response, such as dissolution of a clot. For example, a single bolus can be administered, several divided doses can be administered over time or the dose can be proportionally reduced and administered over a time period by infusion, or increased, as indicated by the exigencies of the therapeutic situation.

One of ordinary skill in the art can determine and prescribe the effective amount of the pharmaceutical composition required. For example, one could start doses at levels lower than that required in order to achieve the desired therapeutic effect and gradually increase the dosage until the desired effect is achieved. In general, a suitable daily dose of a composition of the invention will be that amount of the composition which is the lowest dose effective to produce a therapeutic effect. Such an effective dose will generally depend upon the factors described above. It is preferred that administration be intravenous, intracoronary, intramuscular, intraperitoneal, or subcutaneous.

The invention is further illustrated by the following examples, which should not be construed as further limiting. The contents of all references, pending patent applications and published patents, cited throughout this application, are hereby expressly incorporated by reference.

EXAMPLES

Materials and Methods

The following methodology was used throughout the Examples set forth below. Cloning of $SK_c$ and expression in *E. coli*

These studies were performed by the methods of Reed et al. J. Immunol. 150: 4407–4415 (1993); Reed et al. Biochem. 34:10266–10271 (1995); and Lin et al. Biochem 35: 16879–16885 (1996). To obtain a clone the $SK_c$ gene, bacterial genomic DNA (Sambrook, J. et al., Molecular cloning: a laboratory manual 2nd Ed. Cold Spring Harbor Laboratory Press, N.Y. (1989) was prepared from *Streptococcus equisimilis* strain H46A (Lancefield's Group C, ATCC # 12449) and the $SK_c$ gene was cloned by the polymerase chain reaction (PCR; Saiki, R. et al. Science. 233:1076 (1988)). Two synthetic deoxyoligonucleotide primers were designed based on the published S. equisimilis H46A published $SK_c$ nucleotide sequence (Malke, H. et al. Gene. 34:357 (1985); illustrated in SEQ ID NO: 5). The upstream primer was designed to code for the amino-terminus of the mature peptide and contained an EcoRV restriction site (underlined): 5'-GC GAT ATC GCT GGA CCT GAG TGG (SEQ ID NO: 7). The downstream primer coded for the carboxy terminus of the mature peptide; it contained two stop codons and a 3'Pst1 site (underlined) 5'-GC CTG CAG TCA TTA TTT GTC GTT AGG (SEQ ID NO: 8). Amplified DNA was cut with these enzymes and ligated into a pMal-c vector (New England Biolabs, Beverly, Mass.) for expression in *E. coli* as a factor Xa cleavable fusion protein with maltose binding protein (MBP) on the amino terminus (Maina, C. et al., Gene. 74:365 (1988)). The nucleotide and amino acid sequences of $SK_c$ as a fusion protein with MBP are shown in SEQ ID NO: 1 and SEQ ID NO: 2, respectively. The cloning strategy was designed such that when the MBP-rSK fusion protein was cleaved by factor Xa, the cleaved rSK contained the complete amino acid sequence of $SK_c$ (SEQ ID NO:6) and no other additional residues (Reed et al., J. Immunol. 150:4407–4415 (1993)). Additional amino terminus residues, however, can be added by engineering them into the rSK gene, such that cleavage with Factor Xa produces a novel amino terminus, in order to improve, for example, stability of the rSK derivative.

The pMal-c vector (Maina et al., supra) contains the Ptac promoter which is under the control of the Lac repressor, and which allows induction of fusion protein expression by addition of isopropyl-β-D-thiogalactoside (IPTG) to a culture of cells containing it. The MBP-$SK_c$ protein was purified by amylose affinity chromatography as described (Maina et al., supra (1988); Reed et al.(1993), supra) or by ion-exchange chromatography.

Expression of the $SK_c$ gene in Sf9 cells $SK_c$ was expressed in *Spodoptera frugiperda* insect cells. $SK_c$ was cloned by PCR from genomic DNA (as described above) with different deoxyoligonucleotide primers. These corresponded to the leader peptide (Bgl II restriction site underlined) 5'-CCC AGA TCT ATG AAA AAT TAC TTA TCT TTT GG (SEQ ID NO: 9) and $SK_c$ carboxy terminus (Bam H1 site underlined) 5'-CCC GGA TCC TCA ITA TTT GTC GTT AGG GTT ATC AG (SEQ ID NO: 10). The sequence of this DNA was identical to the published $SK_c$ sequence (shown in SEQ ID NO: 5). $SK_c$ DNA was ligated into a baculovirus transfer vector (pVL1392) for expression in Sf9 cells as described by Summers, M. et al., Texas Agricultural Experiment Station, Bul. No. 1555 (1987) to yield pVL/$SK_c$. The cells were cotransfected by the calcium phosphate method, as modified for insect cells (Summers, et al., supra). Briefly, medium (Grace's medium with 10% fetal bovine serum, FBS) was aspirated from Sf9 cells in 25 cm² flasks (2 million cells) and replaced with 0.75 ml of medium. Then 0.75 ml of transfection buffer (25 mM HEPES, 140 mM NaCl, 125 mM $CaCl_2$, pH 7.1) containing 1 µg of AcMNPV DNA and 2 pg of pVL-$SK_c$ DNA was added dropwise to the flasks. After incubation of cells at 27° C. for 4 h, the medium was removed and the cells were washed with Grace's Medium TNM-FH (10% fetal bovine serum).

The cells were resuspended and applied to microtiter plates at approximately 20,000 cells per well. After 4–6 days of culture the cells were surveyed for microscopic evidence of infection (such as appearance of polyhedra, cytopathic effects, and cell lysis). If infection was evident, supernatants from each well of the microtiter plate were assayed for $SK_c$ antigen by radioimmunoassay as follows. The wells of a microtiter plate were coated with affinity-purified, rabbit polyclonal anti-$SK_c$ monoclonal antibody (mAb; 3 µg/ml, 25 µl, for 1 h). Nonspecific protein binding sites were blocked with 1% bovine serum albumin. Then 25 µl of culture supernatant (or a negative control supernatant) was added to each well for 1 h. After washing, 25 µl of $^{125}$I anti-$SK_c$ mAb (50,000 cpm) was added to the well for an hour. The wells were washed and gamma-counted to determine retention of anti-$SK_c$ mAb. Supernatants from wells displaying evidence of bound $SK_c$ were used to identify positive cultures, which were recloned by transferring limiting dilutions ($10^{-6}$ to $10^{-8}$) into 96-well plates containing growing Sf9 cells. This process was repeated 3 times or until all the screened wells of recloned cultures obtained from an original parent line were positive. Sf9 cells were transfected with purified viral stock and supernatants were harvested. Immunoblotting experiments and activity assays were used to determine that the unpurified recombinant (r)$SK_c$ produced in Sf9 cells had the same molecular mass as wild-type $SK_c$ (47 kDa), reacted with mAbs against wild-type $SK_c$, and was able to form a fully active Pg activator complex.

The bacterial expression system produces an rSK protein preparation that is indistinguishable from $Sk_c$, and is faster and cheaper to produce, thus it is used here preferably for producing rSK and rSK mutants. However, the baculovirus system can prove useful for the expression of SK fragments which appear to be improperly folded as determined by assays of function, extent of circular dichroism, or by binding of conformation-dependent antibodies.

Human plasma clot fibrinolysis induced by rSK and rSK mutants

The fibrinolytic effects of different rSKs was determined in human plasma clot lysis assays as described for SK (Reed G. et al., Proc Natl Acad Sci USA 87: 1114–1118 (1990)). Fresh frozen, pooled citrated human plasma is mixed with trace amounts of $^{125}$I-fibrinogen to achieve approximately 50,000 cpm/50 µl. Then plasma in aliquots of 50 µl was clotted in separate test tubes (12×65 mm) by mixing with a 50 µl solution of thrombin (1 U/ml) and $CaCl_2$ (5 mM) in Tris-buffered saline, pH 7.4. After incubation at 37° C. for 1 hr, the clots were compressed and washed to remove unbound proteins. The radioactivity associated with each clot was measured by use of a gamma scintillation counter. To each tube (in triplicate) were added 100 µl of fresh frozen plasma containing 1 U hirudin/ml, 50 µl of TBS, and 50 µl of rSK (in various concentrations). The tubes were incubated at 37° C. for different time intervals prior to sampling of the supernatant for release of radiolabeled, soluble fibrin degradation products as an indication of fibrinolysis. The percent fibrinolysis was measured as the percent of total $^{125}$I-fibrin radioactivity solubilized during the assay. In certain assays lysis was terminated by the addition of the 100 μl of ice-cold TBS containing the Pn inhibitor aprotinin (5000 k.i.u./ml). The supernatant was sampled and the amount of residual fibrinogen was measured by the sodium sulfite assay (Rampling M. et al., Clin Chim Acta. 67:43–52 (1976)).

EXAMPLE 1
Alteration of the Amino Terminal of SK Regulates the Catalytic Activity of the Activator Complex To determine whether the amino terminus of SK regulates the catalytic function of the activator complex formed between SK and plasminogen, progressive deletion of the amino terminus in recombinant (r) SK molecules was investigated.

To obtain the activation parameters, Glu-plasminogen and samples of each SK indicated in Table 1 were mixed together for 5 min. at 37° C. to make a stoichiometric complex, and assayed as described in Lin, E.-F. et al., Biochem 35:16879–16885 (1996). Briefly, 2–75 nM of the activator complex was added to a cuvette containing various concentrations of Glu-plasminogen (0.3 to 5 of the value of the $K_m$ for SK; Wohl, R. et al. J. Biol. Chem. 255:2005–2013 (1980)) and the substrate S-2251 (0.5 mM) at 37° C. The change in absorbance at 405 nm was monitored at 37° C. in a Hewlett Packard 8451 A diode array spectrophotometer using a thermocycler (model 1136, VWR Scientific, Piscataway, N.J.). Initial reaction rates were obtained from the first 300 sec by plotting A405/time$^2$, and the apparent Michaelis constants and catalytic rate constants were calculated by construction of Lineweaver-Burk plots as outlined (Wohl, supra; Fears, R. et al., Biochem J. 229:555–558 (1985)) or by hyperbolic fits of the data as described (Cleland, W., Meth. Enzymol. 63:103–138 (1979); Robertson, J., KinetAsyst, copyrighted (1989)).

TABLE I

ACTIVATION PARAMETERS

| Type of SK | $K_m$ (μM) | $k_{cat}$ (min$^{-1}$) | $k_{cat}/K_m$ (μM$^{-1}$mi$^{n-1}$) |
|---|---|---|---|
| SK (native) | 0.34 ± 0.07 | 1.37 ± 0.16 | 4.02 |
| rSK 1--414 (full length) | 0.24 ± 0.06 | 2.30 ± 0.41 | 9.85 |
| rSK14-414 | 0.28 ± 0.06 | 1.69 ± 0.27 | 6.08 |
| rSK24-414 | 0.45 ± 0.07 | 0.39 ± 0.03 | 0.87 |
| rSK60-414 | 0.38 ± 0.11 | 0.003 ± (0.001) | ≦0.02 |
| rSK60-414 + rSK1-59 | 0.27 ± 0.07 | 1.19 ± 0.15 | 4.42 |

TABLE 1. Plasminogen activation parameters for various rSKs with NH$_2$-terminal deletions, with Glu-plasminogen.

Results (Table 1) show that alteration of the SK amino terminus (spanning residues 1–59) by deletion markedly impairs indirect plasminogen activation. Thus, full length rSK1-414 has comparable activation parameters ($K_m,k_{cat}$) to commercially available native SK (Table 1). The protein lacking the first 23 amino acid residues, produced by deletion mutation and expression of the deleted SK gene to obtain the rSK24-414 protein, showed a 5.9-fold decrease in $k_{cat}$, compared to that of rSK1-414 protein. Alteration of the first 59 amino acids by deletion to produce mutant rSK60-414 yielded a protein with a 767-fold decrease in $k_{cat}$ compared to that of rSK1-414, without significant change in the $K_m$. Thus, catalysis to activate plasminogen depends on the presence of residues 1–59. Further, mixing rSK60-414 with stoichiometric amounts of the amino terminal fragment rSK1-59 (which is itself inert with respect to Pg), leads to functional complementation between these two molecules, to restore function of an activator complex to obtain nearly the same $k_{cat}$ as the activator complex formed by full length rSK1-414.

These data show that alteration of the SK Amino terminal by deletion of residues 1–23 or 1–59 markedly decreases the catalytic activity of SK activation of Pg, while ability to bind Pg ($K_m$) is unimpaired. The magnitude of the reduction in catalytic activity for Pg activation for the SK protein having a deletion of amino acid residues 1–59 is almost three orders of magnitude, while binding of the Pg substrate is equivalent to that of nSK.

EXAMPLE 2
The SK Amino Terminus Determines the Clot-dependence of Plasminogen Activation by SK SK can form an activator complex that efficiently activates plasminogen in solution in the absence of fibrin, unlike t-PA. However, this property of fibrin-independent plasminogen activation limits the potency of SK as a therapeutic agent for thrombotic diseases, because activation of plasminogen in the blood at sites distant from a thrombus squanders the fibrinolytic effects and thus the therapeutic clot-lysing effects of the molecule.

To test whether the amino terminal peptide comprising amino acid residues 1–59 of SK is involved in the regulation of Pg activation by SK with respect to presence or absence of clots, the clot-lysis ability of equimolar amounts of recombinant full-length rSK1-414, recombinant Amino terminal deletion mutant rSK60-414, and the mixture of fragments rSK1-59+rSK60-414 on the lysis of human plasma clots, as measured by release of $^{125}$I-fibrin, was investigated (see FIG. 1). Since Pg activation by rSK60-414 is 767-fold reduced compared to nSK (see $K_{cat}$, Table 1), it was likely that rSK60-414 would be nearly inactive in promoting clot lysis.

Surprisingly, however, rSK60-414 proved to be almost indistinguishable in its ability to lyse clots from full length rSK1-414, or from the combination of rSK1-59+rSK60-414. These results indicate that, in the presence of fibrin or some other molecule present in the clot in FIG. 1, rSK60-414 efficiently causes Pg activation which does not require the amino acid residues of the amino terminal peptide for efficient indirect plasminogen activation.

EXAMPLE 3
The Amino Terminus Determines the Regulation of Pg Activation by SK in the Presence of Fibrin To identify the component of the clot that enables rSK60-414 to activate Pg, the effects of varying the concentrations of each of the clot components, fibrin and fibrinogen, on ability of the altered Amino terminal deletion mutant rSK60-414 to activate Pg was determined. The presence in the substrate clot of fibrin or fibrinogen can be responsible for allowing indirect plasminogen activation activity of rSK60-414.

To determine plasminogen activation in the presence or absence of fibrin, a soluble fibrin fragment (produced by digestion of fibrin with the snake venom batroxibin, followed by digestion with plasmin, and known as desafib (β$_2$-fibrin 1; American Diagnostica, Greenwich, Conn.) that has been widely employed to study fibrin-dependent plasminogen activation by tissue plasminogen activator, was used here. Glu-plasminogen (300 nM) was mixed with 10 nM rSK60-414 and added to cuvettes containing various amounts of human fibrin fragments or fibrinogen (0–2 μM), 0.5 mM of substrate (H-D-valyl-L-leucyl-L-lysine-p-nitroanalide dihydrochloride) in assay buffer (50 mM Tris-HCl, 100 mM NaCl, pH 7.4) at 37° C.

Figure 2:
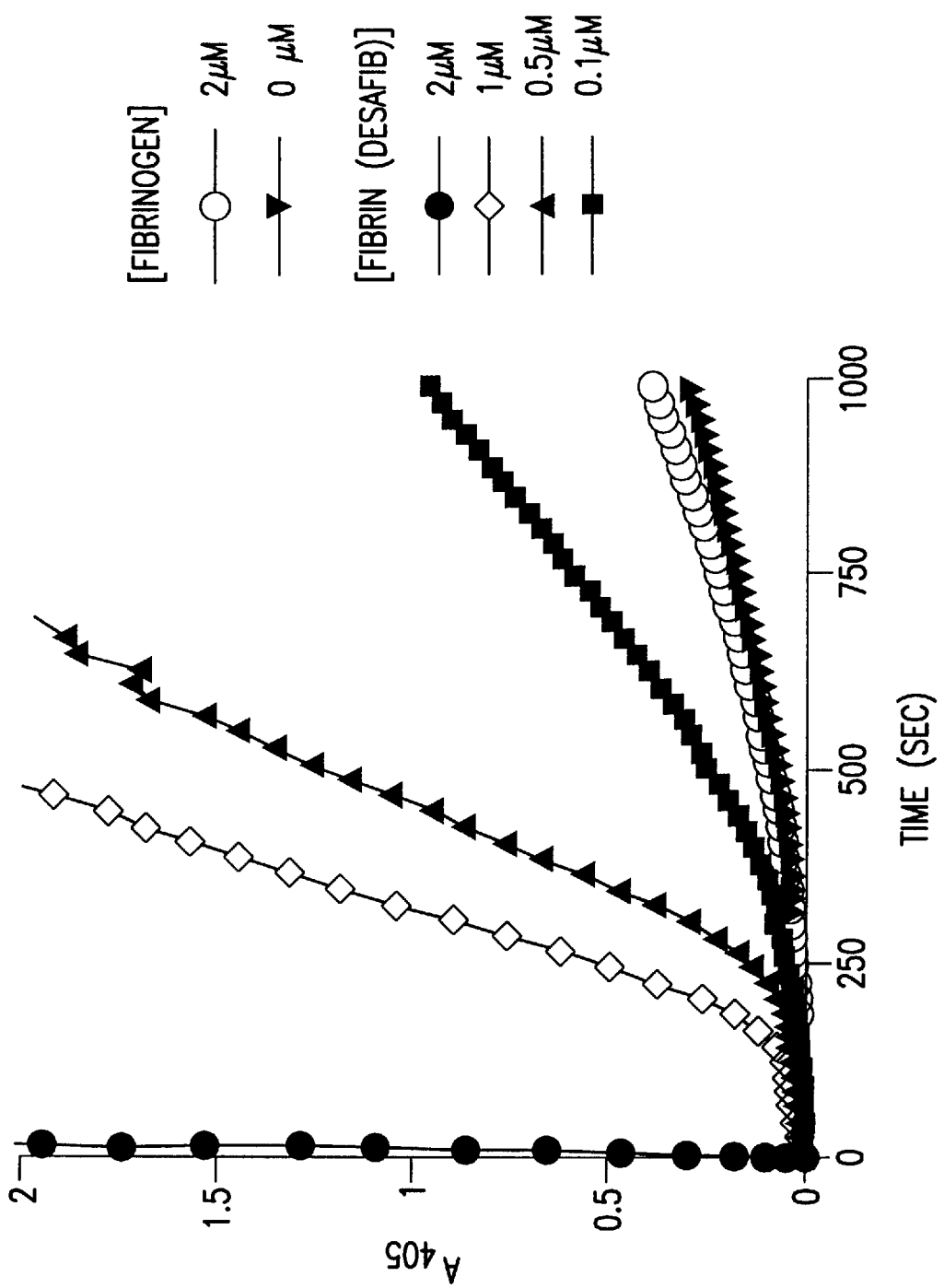
FIG. 2 is a graph which shows the effect of fibrinogen and soluble fibrin fragments (desafib) on the activation of Glu-plasminogen by rSK60-414. Plasminogen activation was detected as increase of absorbance at 405 nm.

The results (FIG. 2) show that the rate of plasminogen activation increased markedly as a function of increasing the amounts of the desafib fibrin substrate. In contrast, even at the highest doses of fibrinogen (American Diagnostica), rSK60-414 had little function to activate the complex formed by rSK60-414 and Pg (FIG. 2; only the highest 2 μM fibrinogen dose is shown for clarity).

These findings indicate that the amino terminus of SK regulates the catalytic efficiency of the activator complex for plasminogen substrates, such that alteration, e.g., removal of the amino terminus, converts SK to a fibrin-dependent, t-PA-like thrombolytic molecule.

EXAMPLE 4
Clot Lysis and Fibrinogen Sparing by rSK60-414 Under Physiological Conditions.

The ability of fibrin-dependent t-PA-like recombinant SK rSK60-414 to lyse a clot in the presence of excess human plasma was compared to that of full length rSK1-414. Clot dissolution was measured in 2 ml of human plasma containing 10 μM thrombin inhibitor PPACK (D-phe-pro-arg chloromethylketone; Calbiochem, Calif.), and is shown as percent fibrinolysis in FIG. 3, left hand panel.

The data show that the t-PA-like rSK60-414 (rSKΔ59) caused 85–90% dissolution of the clot at 25 and 50 nM, significantly greater than that seen with full length rSK. At lower concentrations (12.5 nM and 6.25 nM) substantial clot lysis was observed, in contrast almost none produced by rSK.

Figure 3A:
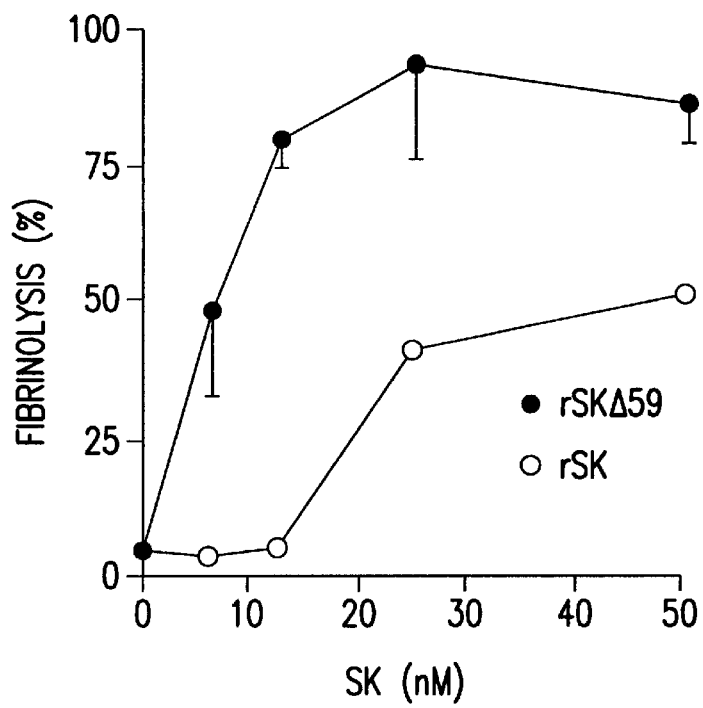
FIG. 3 is a set of graphs which show that streptokinase with a deletion of amino terminal 1–59 amino acid residues dissolves clots under physiological conditions (left panel), and that enhanced degradation of fibrinogen has not occurred in the supernatants from clot dissolution from the deletion SK (right panel).
Figure 3B:
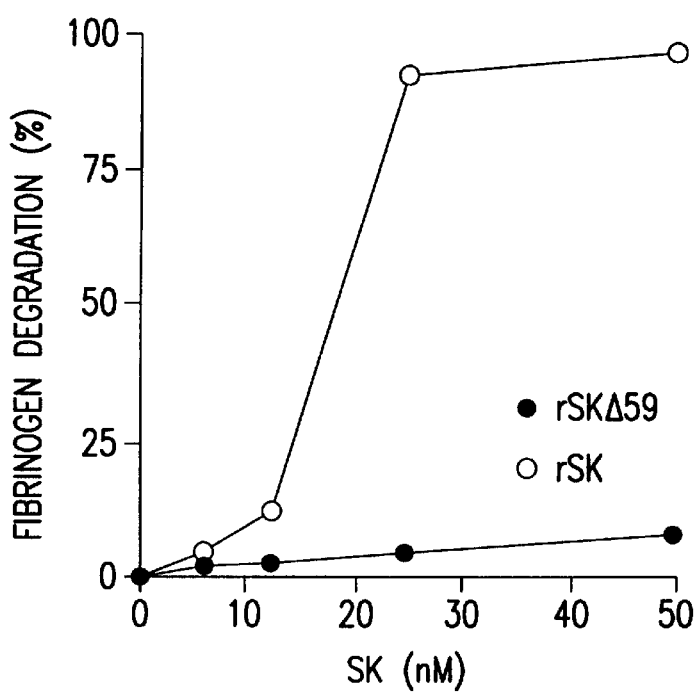

Further, fibrinogen present in human plasma was not degraded by rSK60-414 (rSKΔ59) in contrast to rSK, which produced quantitative loss (greater than 95%) of fibrinogen (FIG. 3, right panel). By virtue of its requirement for fibrin for Pg activation in human plasma, and it sparing of fibrinogen during clot dissolution, SK deleted of amino terminal amino acid residues is similar to t-PA.

EQUIVALENTS

Those skilled in the art will recognize, or be able to ascertain using no more than routine experimentation, many equivalents to the specific embodiments of the invention described herein. Such equivalents are intended to be encompassed by the following claims.

Other embodiments are within the following claims.

---

What is claimed is:

1. A composition for dissolving blood clots in a subject, comprising an isolated genetically modified substantially pure streptokinase in a pharmaceutically acceptable carrier, the streptokinase capable under physiological conditions of plasminogen activation in the presence but not the absence of fibrin, and that induces, under physiological conditions, dissolution of fibrin in a clot while sparing fibrinogen in the plasma, wherein the modification of streptokinase is a mutational alteration such that the amino terminus is selected from the group consisting of amino acid residues 24, 59, 60, 65, 144, and 149 of SEQ ID NO: 6.

2. An effective dose of a composition according to claim 1.

3. A composition according to claim 1, wherein activation of plasminogen is at least fifty-fold greater in the presence of fibrin than in the absence of fibrin.

4. A composition according to claim 3, wherein activation of plasminogen is at least hundred-fold greater in the presence than in the absence of fibrin.

5. A composition according to claim 1, wherein the genetically modified streptokinase is produced as a fusion protein.

6. A composition according to claim 5, wherein the protein is produced as a fusion having at its amino terminus the maltose binding protein.

7. A composition according to claim 1 having a carboxy terminus selected from the group consisting of amino acid residues 293, 386 and 414.

8. A composition comprising an effective dose of an isolated genetically modified substantially pure streptokinase, the modification being deletion of amino acid residues in the amino terminus, wherein the modified streptokinase is a fibrin-dependent plasminogen activator having an amino terminus selected from the group consisting of amino acid residues 24, 59, 60, 65, 144, and 149 of SEQ ID NO: 6, and that induces, under physiological conditions, dissolution of fibrin in a clot while sparing fibrinogen in the plasma.

9. A recombinantly produced substantially pure streptokinase having a deletion of the amino terminus of SEQ ID NO: 6, wherein the deletion extends from residue 1 through residue 23 to residue 148, such that the amino terminus of the streptokinase is selected from the group consisting of any of residues 24 through 149 of SEQ ID NO: 6, the modified streptokinase capable under physiological conditions of activating plasminogen only in the presence of a clot, while sparing fibrinogen in the plasma.

10. A recombinantly produced modified streptokinase according to claim 9, wherein the carboxy terminus is selected from the group consisting of residues 293, 386 and 414 of SEQ ID NO: 6.

11. An effective dose of a recombinantly produced modified streptokinase according to claim 9, wherein antigenic residues are genetically deleted to diminish reactivity with antibodies in a human subject.

* * * * *